(12) United States Patent
Lahousse et al.

(10) Patent No.: US 11,351,105 B2
(45) Date of Patent: Jun. 7, 2022

(54) COMPOSITION COMPRISING ALKYLCELLULOSE, INCOMPATIBLE HYDROCARBON AND SILICONE OILS AND METHOD EMPLOYING IT

(71) Applicant: L'OREAL, Paris (FR)

(72) Inventors: Florence Lahousse, Chevilly la Rue (FR); Emilie Henin, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/060,059

(22) PCT Filed: Dec. 15, 2016

(86) PCT No.: PCT/EP2016/081260
§ 371 (c)(1),
(2) Date: Jun. 7, 2018

(87) PCT Pub. No.: WO2017/108584
PCT Pub. Date: Jun. 29, 2017

(65) Prior Publication Data
US 2019/0015314 A1    Jan. 17, 2019

(30) Foreign Application Priority Data

Dec. 21, 2015   (FR) ........................................ 1562905
Dec. 21, 2015   (FR) ........................................ 1562906

(51) Int. Cl.
| | |
|---|---|
| *A61K 8/891* | (2006.01) |
| *A61K 8/73* | (2006.01) |
| *A61K 8/34* | (2006.01) |
| *A61Q 1/06* | (2006.01) |
| *A61K 8/92* | (2006.01) |
| *A61Q 19/00* | (2006.01) |
| *A61Q 1/04* | (2006.01) |

(52) U.S. Cl.
CPC .............. *A61K 8/731* (2013.01); *A61K 8/342* (2013.01); *A61K 8/891* (2013.01); *A61K 8/92* (2013.01); *A61Q 1/04* (2013.01); *A61Q 1/06* (2013.01); *A61Q 19/00* (2013.01); *A61K 2800/31* (2013.01); *A61K 2800/436* (2013.01); *A61K 2800/5922* (2013.01)

(58) Field of Classification Search
None
See application file for complete search history.

(56) References Cited

U.S. PATENT DOCUMENTS

| | | |
|---|---|---|
| 2,230,063 A | 1/1941 | Klimist et al. |
| 3,787,337 A | 1/1974 | Goodwin |
| 4,683,134 A | 7/1987 | Palinczar |
| 4,699,779 A | 10/1987 | Palinczar |
| 4,795,631 A | 1/1989 | Sheehan |
| 4,797,273 A | 1/1989 | Linn et al. |
| 5,641,493 A | 6/1997 | Date et al. |
| 5,665,368 A | 9/1997 | Lentini et al. |
| 5,674,508 A | 10/1997 | Deserable |
| 5,747,001 A | 5/1998 | Wiedmann |
| 5,747,013 A | 5/1998 | Mougin et al. |
| 5,849,834 A | 12/1998 | Matsuzaki et al. |
| 5,908,631 A | 6/1999 | Arnaud et al. |
| 6,001,374 A | 12/1999 | Nichols |
| 6,039,960 A | 3/2000 | Chung et al. |
| 6,362,353 B1 | 3/2002 | Ellis |
| 6,387,405 B1 | 5/2002 | Shah et al. |
| 7,534,446 B2 * | 5/2009 | Rando .................... A61K 8/342 424/401 |
| 2002/0015683 A1 | 2/2002 | Nichols et al. |
| 2002/0022009 A1 | 2/2002 | Poterie et al. |

(Continued)

FOREIGN PATENT DOCUMENTS

| | | |
|---|---|---|
| CN | 103384511 A | 11/2013 |
| DE | 31 12943 A1 | 10/1982 |

(Continued)

OTHER PUBLICATIONS

International Search Report dated Mar. 3, 2017 in PCT/EP2016/081260 filed Dec. 15, 2016.

(Continued)

*Primary Examiner* — Craig D Ricci
(74) *Attorney, Agent, or Firm* — Oblon, McClelland, Maier & Neustadt, L.L.P.

(57) ABSTRACT

The present invention is relating to a cosmetic composition comprising: —at least 2% by weight, with respect to the weight of the composition, of alkylcellulose, the alkyl residue of which comprises between 2 and 6 carbon atoms, preferably between 2 and 3, —at least one non-volatile polar hydrocarbon first oil, —at least 20% by weight, with respect to the weight of the composition, of at least one second oil, incompatible with the first oil or oils, chosen from non-volatile silicone oils, from non-volatile fluorinated oils, or their combinations, —optionally at least one non-volatile third oil, different from the first oil or oils, chosen from polar or non-polar hydrocarbon oils, silicone oils different from the second oil or oils, phenylated oils not comprising a dimethicone fragment, or their mixtures, —less than 5% by weight of water, with respect to the weight of the composition. The composition can comprise at least one wax. The invention also relates to a method for making up and/or caring, in particular for the lips, in which the abovementioned composition is applied.

15 Claims, No Drawings

(56) References Cited

U.S. PATENT DOCUMENTS

| | | |
|---|---|---|
| 2002/0127192 A1 | 9/2002 | Murphy |
| 2003/0077962 A1 | 4/2003 | Krzysik et al. |
| 2004/0081633 A1 | 4/2004 | Mercier et al. |
| 2004/0197284 A1 | 10/2004 | Auguste |
| 2005/0008667 A1 | 1/2005 | Liechty et al. |
| 2005/0238979 A1 | 10/2005 | Dumousseaux |
| 2005/0244442 A1 | 11/2005 | Sabino et al. |
| 2005/0276763 A1 | 12/2005 | Pfeifer et al. |
| 2006/0013789 A1 | 1/2006 | Blin et al. |
| 2006/0019848 A1 | 1/2006 | Luo et al. |
| 2006/0088483 A1 | 4/2006 | Thevenet |
| 2006/0275226 A1 | 12/2006 | Dahms |
| 2007/0104667 A1 | 5/2007 | Mondet |
| 2009/0098068 A1 | 4/2009 | Takakura |
| 2009/0317344 A1 | 12/2009 | Zhang |
| 2011/0038820 A1 | 2/2011 | Barba et al. |
| 2011/0147999 A1 | 6/2011 | Luo et al. |
| 2013/0045913 A1 | 2/2013 | Germaneau et al. |
| 2013/0046029 A1 | 2/2013 | Germaneau et al. |
| 2013/0280197 A1* | 10/2013 | Geffroy .................. A61K 8/342 424/64 |
| 2013/0280198 A1 | 10/2013 | Cavazutti et al. |
| 2020/0146968 A1 | 5/2020 | Cavazutti et al. |

FOREIGN PATENT DOCUMENTS

| | | |
|---|---|---|
| DE | 698 32 545 T2 | 9/2006 |
| EP | 0 336 902 A2 | 10/1989 |
| EP | 0 795 318 A2 | 9/1997 |
| EP | 0 823 250 A2 | 2/1998 |
| EP | 0 861 657 A2 | 9/1998 |
| EP | 1 051 968 A2 | 11/2000 |
| EP | 1 192 937 A2 | 4/2002 |
| EP | 1 604 635 A2 | 12/2005 |
| EP | 1 604 644 A1 | 12/2005 |
| EP | 1 913 929 A2 | 4/2008 |
| EP | 2 116 221 A1 | 11/2009 |
| EP | 2 599 472 B1 | 11/2016 |
| FR | 2 771 628 A1 | 6/1999 |
| FR | 2 771 629 A1 | 6/1999 |
| FR | 2 918 272 | 1/2009 |
| FR | 2 964 868 A1 | 3/2012 |
| FR | 2 921 266 B1 | 6/2012 |
| FR | 2 978 037 B1 | 1/2014 |
| GB | 795841 | 5/1958 |
| JP | H10-067624 | 3/1998 |
| JP | 2000-219617 A | 8/2000 |
| KR | 10-2010-0103708 A | 9/2010 |
| WO | WO 96/36310 | 11/1996 |
| WO | WO 2005/046626 A2 | 5/2005 |
| WO | WO 2006/017203 A1 | 2/2006 |
| WO | WO 2007/026101 A1 | 3/2007 |
| WO | WO 2009/006218 A2 | 1/2009 |
| WO | WO 2009/080953 A2 | 7/2009 |
| WO | WO 2009/080958 A2 | 7/2009 |
| WO | WO 2009/105294 A2 | 8/2009 |
| WO | WO 2011/100275 A1 | 8/2011 |
| WO | WO 2012/038879 A2 | 3/2012 |
| WO | WO 2012/064714 A2 | 5/2012 |
| WO | WO 2013/088051 A2 | 6/2013 |
| WO | WO 2013/102727 A1 | 7/2013 |
| WO | WO 2014/097258 A2 | 6/2014 |
| WO | WO 2015/014789 * | 2/2015 ............... A61K 8/34 |
| WO | WO 2015/014789 A1 | 2/2015 |

OTHER PUBLICATIONS

"Maxigloss™ Plus," Resources of Nature, Inc., Sep. 26, 2012, 2 total pages, XP002755943.
Susan C. Smolinske "Handbook of Food, Drug, and Cosmetic Excipients" CRC Press LLC, 1992, p. 231 (with cover pages).
"Glossy Full Couleur Extreme Shine Lip Gloss", Make Up For Ever, Product No. 1522027, Mar. 2011, 3 pages.
Marie Contier et al., "Characterization of the tack and gloss of cosmetic formulations", LVMH Recherche Parfums & Cosmetiques Materials Innovation Department, May 13, 2016, pp. 1-5 (with English translation).
Written Opinion dated Jul. 21, 2008, in French Patent Application No. 0854940.
"Basic Properties of PARLEAM®", NOF Corporation Oleo & Specialty Chemicals Div., Apr. 2015, 2 pages.
"Report on tests carried out by the company L'Oréal in response to the notice of opposition formed by the company Parfums Christian Dior against patent EP 2 618 803 B1", L'Oréal, Jun. 19, 2017, pp. 1-3 (with English translation).
"Ethocel", Ethylcellulose Polymers Technical Handbook, Dow Cellulosics, Sep. 2005, pp. 1-28.
Charles M. Hansen, "The Three Dimensional Solubility Parameter—Key to Paint Component Affinities: I. Solvents, Plasticizers, Polymers, and Resins", Journal of Paint Technology, vol. 39, No. 505, Feb. 1967, pp. 104-117.
Notice of Opposition issued Jan. 6, 2017 in European Patent Application No. 2 618 803 B1 (with English translation).
Response to Notice of Opposition issued Jun. 19, 2017 in European Patent Application No. 2 618 803 (with English translation).
Oct. 21, 2015, Notice of Opposition issued in European Application No. 2 618 811.
Nov. 4, 2015 Office Action issued in U.S. Appl. No. 13/824,533.
Mar. 11, 2016 Office Action issued in U.S. Appl. No. 13/824,548.
Mar. 31, 2016 Office Action issued in U.S. Appl. No. 14/370,335.
Oct. 8, 2015 Office Action issued in U.S. Appl. No. 14/370,335.
EWG, "Polysorbate-60", printed 2019.
Chemical Book, Mineral Oil, pp. 1-2 (Nov. 20, 2018) (Year:2018).
"Colour Gloss Extension", Mintel No. 10116327, Aug. 2002, 2 pages.
McLain, "Final Report of the Cosmetic Ingredient Review Expert Panel on the Safety Assessment of Polyisobutene and Hydrogenated Polyisobutene as Used in Cosmetics", International Journal of Toxicology, 27 (Suppl. 4) pp. 83-106, 2008.
Melzer et al., "Ethylcellulose: a new type of emulsion stabilizer," European Journal of Pharaceutics and Biopharmaceuticals, 56:23-27, 2003.
Wikipedia, "Talk:polybutene" 2012; https://en.wikipedia.org/wiki/Talk%3APolyubutene.
"Smooth Cover Gel," Database GNPD [Online] Mintel, Sep. 2009, XP-002658176, pp. 1-2.
"Mousse Foundation Natural Bronzing Effect," Database GNPD [Online] Mintel, Nov. 2010, XP-002658177, pp. 1-2.
"Ceramide Moisture Network Night Cream [Ingredients]," Database GNPD [Online] Mintel, Sep. 2004, XP-002658178, pp. 1-2.
"Beauty Body Gel," Database GNPD [Online] Mintel, Sep. 2010, XP-002658179, pp. 1-2.
"Butter Shine Lipstick," Database GNPD [Online] Mintel, Oct. 2008, XP-002658180, pp. 1-2.
"Lip Polish," Database GNPD [Online] Mintel, Jun. 2010, XP-002658181.
"Liquid Foundation," Database GNPD [Online] Mintel, Sep. 2010, XP-002658182.
May 6, 2011 French Search Report and Written Opinion issued in French Patent Application No. FR 1057526 (with translation).
May 6, 2011 French Search Report and Written Opinion issued in French Patent Application No. FR 1057528 (with translation).
Sep. 5, 2011 French Search Report and Written Opinion issued in French Patent Application No. FR 1060600 (with translation).
Sep. 5, 2011 French Search Report and Written Opinion issued in French Patent Application No. FR 1060650 (with translation).
Sep. 5, 2011 French Search Report and Written Opinion issued in French Patent Application No. FR 1060652 (with translation).
Apr. 3, 2012 Written Opinion of the International Searching Authority issued in International Application No. PCT/182011/054087.
Mar. 26, 2013 International Preliminary Report on Patentability issued in International Application No. PCT/IB2011/054087.
Apr. 3, 2012 International Search Report issued in International Application No. PCT/IB2011 /054087.
International Search Report issued in International Patent Application No. PCT/EP2011/066208 dated Mar. 29, 2012.

(56) References Cited

OTHER PUBLICATIONS

International Preliminary Report on Patentability issued in International Patent Application No. PCT/EP2011/066208 dated Mar. 26, 2013.
Mar. 10, 2014 Office Action issued in U.S. Appl. No. 13/824,548.
Feb. 13, 2014 Office Action issued in U.S. Appl. No. 13/824,548.
Oct. 31, 2012 French Search Report and Written Opinion issued in French Patent Application 1250017 (with English Translation).
Dec. 24, 2014 Office Action issued in Japanese Application No. 2013-528824. (with English Translation).
Flirt-Tinis Protective Lip Balm, XP-002731953, Sep. 2008, pp. 1-3.
Makingcosmetics.com article "Making emulsions for cosmetics," dated Oct. 12, 2004.
Google date for makingcosmetics.com article printed 2014.
Wikipedia, Hydrocarbon, (accessed Feb. 26, 2015) pp. 1-5.
Wikipedia, Triethanolamine, (accessed Feb. 26, 2015) pp. 1-6.
SAAPedia, Octyldodecyl stearoyl stearate (Oct. 28, 2014) pp. 1-2.
Love to Know Makeup (Jun. 11, 2008), pp. 1-4 (Year: 2008).
Chemical Land, Dihydroxyacetone accessed Jun. 6, 2019, pp. 1-2 (Year:2019).
European Food Safety Authority, Mineral Oil Hydrocarbon, (Jun. 6, 2012) pp. 1-2 (Year:2012).
Mar. 10, 2015 Office Action issued in Chinese Application No. 201180055831.3.
Why balsam and vanishing cream in the cosmetics are classified as "water-in-oil" type and a "oil-in-water" type?, 2015.
Arbonne product "Lip Polish", Technical document.
Tendertones SPF 12 (Purring), XP-002731954, Aug. 2007, pp. 1-2.
Lip Moisture Cream SPF 30, XP-002731955, Apr. 2006, pp. 1-3.
Nov. 13, 2014 Search Report and Written Opinion issued in French Application No. 1452985.
Nov. 14, 2013 Office Action issued in Korean Application No. 10-2013-7018815.
Nov. 28, 2013 Office Action issued in Korean Application No. 10-2013-7021162.
"Making Emulsions for Cosmetics," makingcosmetics.com, Oct. 12, 2004.
Google search results for "cosmetic and emulsion," Nov. 30, 2014.
Mar. 11, 2015 Office Action issued in U.S. Appl. No. 13/824,533.
Dec. 18, 2014 Office Action issued in U.S. Appl. No. 13/824,548.
"Colour Gloss Extension", Clarins, Product No. 10116327, Aug. 2002.

* cited by examiner

COMPOSITION COMPRISING ALKYLCELLULOSE, INCOMPATIBLE HYDROCARBON AND SILICONE OILS AND METHOD EMPLOYING IT

A subject-matter of the present invention is a composition, intended in particular for making up and/or caring for the lips, comprising alkylcellulose, optionally at least one wax, and a mixture of oils, two at least of which are incompatible with one another. Another subject-matter of the invention is a method for making up and/or caring, in particular for the lips, consisting in applying such a composition to the lips.

The present invention is more particularly concerned with compositions for making up and/or caring for the lips for which a glossy deposited layer is obtained.

Liquid or solid anhydrous compositions, dedicated in particular to making up and/or caring for the lips, with a glossy result, are obtained from mixtures comprising relatively high contents of oils, and also colourants, such as, for example, pearlescent agents and/or pigments In the case of fluid compositions, they have to exhibit a viscosity sufficient to guarantee stability of the composition over time, in particular to keep the colourants in suspension and to prevent the composition from flowing out of the areas to be treated or to be made up during application. The viscosity of the composition must also limit the migration of the latter into the wrinkles and fine lines of the outline of the lips after application. However, this viscosity must remain such that the composition can be applied satisfactorily, with good slip, in order to obtain a homogeneous deposited layer which is sufficiently thin.

In the case of solid compositions, structuring agents, such as, for example, waxes, are often added to the abovementioned mixtures. These compounds have to sufficiently stiffen the compositions for them to be able to be moulded in the stick form, without harming their properties of use. This is because the compositions have to be capable of being destructured in order to make possible the ready application of an appropriate amount to the lips.

Whatever the liquid or solid formulation form, in view of the large amount of oils, in particular non-volatile oils, present, these compositions often contain thickening agents, like fillers, such as, for example, bentones or silicas. The disadvantage of this type of compound is that it reduces the gloss of the resulting deposited layer. Furthermore, when they are employed in excessively great contents, the compositions can become uncomfortable and can give sensations of dryness or of tightness of the lips.

Polymers may also be employed, such as, for example, cellulose ethers, as is described in the document U.S. Pat. No. 5,908,631.

However, the wear property of the gloss, and also the resistance to the transfer of the colour, of the compositions described can be further improved.

This is because women are increasingly looking for compositions having a deposited layer which is persistent, in particular retaining its gloss characteristics, with a limited transfer of colour, without, however, damaging the properties of comfort of the deposited layer, which has to be non-tacky or only very slightly tacky, and must not provide a feeling of tightness or dryness of the lips once the composition is applied.

The present invention thus has the object of solving the above problems and relates to a composition comprising, in a physiologically acceptable medium:

- at least 2% by weight, with respect to the weight of the composition, of alkylcellulose, the alkyl residue of which comprises between 2 and 6 carbon atoms, preferably between 2 and 3,
- at least one non-volatile polar hydrocarbon first oil,
- at least 20% by weight, with respect to the weight of the composition, of at least one second oil, incompatible with the first oil or oils, chosen from non-volatile silicone oils, from non-volatile fluorinated oils, or their combinations,
- optionally at least one non-volatile third oil, different from the first oil or oils, chosen from polar or non-polar hydrocarbon oils, silicone oils different from the second oil or oils, phenylated oils not comprising a dimethicone fragment, or their mixtures,
- less than 5% by weight of water, with respect to the weight of the composition.

The composition can additionally comprise at least one wax.

The invention also relates to a method for making up and/or caring, in particular for the lips, in which the abovementioned composition is applied.

The composition according to the invention exhibits the advantage of being stable over time, being easy to apply and giving a homogeneous, non-tacky deposited layer.

In addition, the composition according to the invention gives a glossy deposited layer with an improved wear property of the gloss over time.

Furthermore, the deposited layer obtained by application of the composition according to the invention is virtually resistant, indeed even resistant, to the transfer of the colour and additionally exhibits an improved resistance to migration.

In that which will follow, the expression "at least one" is equivalent to "one or more".

The expressions "between . . . and . . . ", "of between . . . and . . . " and "ranging from . . . to . . . " should be understood as meaning limits included, unless otherwise specified.

The temperatures mentioned in the description are shown at atmospheric pressure ($1.013 \times 10^5$ Pa).

The cosmetic composition according to the invention advantageously comprises a physiologically acceptable medium, that is to say a medium which is particularly suitable for the application of a composition of the invention to the lips.

The physiologically acceptable medium is generally adapted to the nature of the support onto which the composition has to be applied, and also to the appearance under which the composition has to be packaged.

The composition according to the invention comprises less than 5% by weight of water, more particularly less than 2% by weight of water, with respect to the weight of the composition, and is advantageously anhydrous.

"Anhydrous" is understood in particular to mean that water is preferably not deliberately added to the composition but may be present in the trace form in the various compounds used.

The composition according to the invention is advantageously provided in a fluid (gloss) or pasty form.

When the composition according to the invention comprises at least one wax, it can advantageously be provided in a fluid (gloss) to solid (stick) form.

"Fluid" is understood in particular to mean a composition which is not solid at ambient temperature (25° C.) and for which it is possible to measure a viscosity.

"Solid" is understood in particular to mean a composition, the hardness of which can be measured according to the "cheese wire" method.

Intermediate textures are found between these two extremes, neither the viscosity of which nor the hardness of which can be measured according to the methods described in detail below. Such compositions are then described as pastes.

Protocol for Measuring the Viscosity:

The measurement of the viscosity is generally carried out at 25° C., using a Rheomat RM180 viscometer equipped with a No. 3 spindle or with a No. 4 spindle, according to the working recommendations, the measurement being carried out after 10 minutes of rotation of the spindle in the composition (after which time stabilization of the viscosity and of the rate of rotation of the spindle are observed), at a rate of 200 revolutions/min.

Preferably, the composition exhibits, at 25° C., a viscosity of between 0.1 and 25 Pa·s and preferably of between 0.5 and 22 Pa·s.

Protocol for Measuring the Hardness:

The composition in stick form is stored at 20° C. for 24 hours before measuring the hardness. The measurement is carried out at 20° C. and consists in transversely cutting a stick of product, which is preferably a circular cylinder, by means of a rigid tungsten wire with a diameter of 250 μm, by moving the wire relative to the wand at a rate of 100 mm/min.

The hardness of the samples of compositions of the invention, expressed in $Nm^{-1}$, is measured using a DFGS2 tensile testing device sold by Indelco-Chatillon.

The measurement is repeated three times and then averaged. The average of the three values read using the above-mentioned tensile testing device, noted Y, is given in grams. This average is converted into newtons and then divided by L, which represents the greatest distance through which the wire passes. In the case of a cylindrical stick, L is equal to the diameter (in metres).

The hardness is converted into $Nm^{-1}$ by the equation below:

$$(Y \times 10^{-3} \times 9.8)/L$$

According to this measurement method, the composition according to the invention, when it is in solid form, advantageously exhibits a hardness at 20° C. and at atmospheric pressure of between 20 and 150 $Nm^{-1}$ and preferably between 40 and 120 $Nm^{-1}$.

Alkycellulose

As indicated above, the composition according to the invention comprises alkylcellulose, the alkyl residue of which comprises between 2 and 6 carbon atoms, in particular between 2 and 3 carbon atoms.

The alkylcellulose is a cellulose alkyl ether comprising a chain consisting of β-anhydroglucose units bonded together via acetal bonds. Each anhydroglucose unit exhibits three replaceable hydroxyl groups, all or some of these hydroxyl groups being able to react according to the following reaction:

RONa+R'Cl→ROR'+NaCl, where R represents a cellulose radical and R' represents a $C_2$-$C_6$ alkyl radical.

Advantageously, the alkylcellulose can be chosen from ethylcellulose and propylcellulose, and preferably ethylcellulose.

Total substitution of the three hydroxyl groups would lead, for each anhydroglucose unit, to a degree of substitution of 3, in other words to a content of alkoxy groups of 54.88%.

The ethylcellulose polymers used in a cosmetic composition according to the invention are preferably polymers exhibiting a degree of substitution with ethoxy groups ranging from 2.5 to 2.6 per anhydroglucose unit, in other words comprising a content of ethoxy groups ranging from 44% to 50%.

The alkylcellulose employed in the composition according to the invention is more particularly in the pulverulent form.

It is, for example, sold under the "Ethocel Standard" trade names of Dow Chemicals, with in particular "Ethocel Standard 7 FP Premium" and "Ethocel Standard 100 FP Premium". Other commercially available products, such as those sold by Ashland Inc. under the Aqualon Ethylcellulose type K, type N and type T names, preferably type N names, such as N7 or N100, are particularly suitable for the implementation of the invention.

Advantageously, the content of alkylcellulose varies from 2% to 16% by weight, more particularly from 4% to 16% by weight and preferably from 4% to 10% by weight, with respect to the weight of the composition.

First Non-Volatile Hydrocarbon Oils

As indicated above, the composition according to the invention comprises at least one non-volatile polar hydrocarbon first oil.

"Oil" is understood to mean a water-immiscible non-aqueous compound which is liquid at ambient temperature (25° C.) and atmospheric pressure ($1.013 \times 10^5$ Pa).

"Immiscible" is understood to mean that the mixing of the same amount of water and oil, after stirring, does not result in a stable solution comprising only a single phase, under standard temperature and pressure conditions. Observation is carried out by eye or using a phase contrast microscope, if necessary, on 100 g of mixture obtained after sufficient Rayneri stirring to produce a vortex within the mixture (by way of indication, 200 to 1000 rev/min), the resulting mixture being left standing, in a closed flask, for 24 hours at ambient temperature before observation.

"Hydrocarbon oil" is understood to mean an oil formed essentially of, indeed even consisting of, carbon and hydrogen atoms, and optionally of oxygen and nitrogen atoms, and not containing a silicon or fluorine atom.

The hydrocarbon oil is thus distinct from a silicone oil and a fluorinated oil.

It can contain alcohol, ester, ether, carboxylic acid, amine and/or amide groups.

A polar oil within the meaning of the invention comprises, besides the carbon and hydrogen atoms, at least one oxygen or nitrogen atom and preferably at least one oxygen atom.

"Non-volatile" is understood to mean an oil, the vapour pressure at 25° C. and atmospheric pressure of which is non-zero and less than 2.66 Pa (0.02 mmHg) and better still less than 0.13 Pa ($10^{-3}$ mmHg).

More particularly, this or these first oils comprise at least one hydroxyl unit or at least one ester unit or also their combinations.

The first oil(s) are furthermore chosen from oils which are incompatible with the silicone or fluorinated second oil(s). In order to confirm this nature, the compatibility protocol described below is employed.

Tests of Compatibility of the Oils

The preparation is carried out of three mixtures of 100 g each comprising two oils in the following proportions: 75/25, 50/50 and 25/75, at 95° C. under Rayneri stirring sufficient to produce a vortex within the mixture (by way of indication, 200 to 1000 rev/min) for one hour. Each resulting mixture is poured into a container which is closed. The composition is left at ambient temperature for 24 hours.

The resulting mixture is subsequently observed by eye and, if need be, with a phase contrast microscope.

If the mixture produces two phases, completely or partially separated (two oils with a clean separation or else separated by a region comprising a mixture of the two), then the two oils are said to be incompatible at the proportions given.

If the mixture of the two oils appears homogeneous by eye, opaque or transparent, and if observation with a phase contrast microscope reveals a mixture of two oils, the oils are said to be incompatible at the proportions given.

In the other cases, the oils are said to be compatible.

Mention may be made, among the non-volatile polar hydrocarbon oils which can be used as first oil in the context of the present invention, of $C_{10}$-$C_{26}$ alcohols; non-aromatic, saturated or unsaturated, linear or branched mono- or diesters comprising up to 30 carbon atoms and optionally comprising one or two ether groups; aromatic mono- or diesters comprising up to 30 carbon atoms and optionally comprising one or two ether groups; non-aromatic, saturated or unsaturated, linear or branched triesters comprising less than 60 carbon atoms and optionally comprising one to three ether groups; vegetable oils; and their mixtures.

$C_{10}$-$C_{26}$ alcohols, preferably monoalcohols.

More particularly, the $C_{10}$-$C_{26}$ alcohols are saturated or unsaturated and branched or unbranched and comprise from 10 to 26 carbon atoms.

Advantageously, the $C_{10}$-$C_{26}$ alcohols are fatty alcohols, which are preferably branched when they comprise at least 16 carbon atoms.

Mention may be made, as examples of fatty alcohols which can be used according to the invention, of linear or branched fatty alcohols of synthetic origin or alternatively of natural origin, such as, for example, alcohols derived from plant materials (coconut, palm kernel, palm, and the like) or animal materials (tallow, and the like).

Use may also be made of other long-chain alcohols, such as, for example, ether alcohols or alternatively "Guerbet" alcohols.

Finally, use may also be made of certain more or less long fractions of alcohols of natural origin, such as, for example, coconut ($C_{12}$ to $C_{18}$) or tallow ($C_{16}$ to $C_{18}$).

Use is preferably made of a fatty alcohol comprising from 10 to 24 carbon atoms and more preferably from 12 to 22 carbon atoms.

Mention may in particular be made, as specific examples of fatty alcohols which can preferably be used, of lauryl alcohol, isostearyl alcohol, oleyl alcohol, 2-butyloctanol, 2-undecylpentadecanol, 2-hexyldecyl alcohol, isocetyl alcohol, octyldodecanol and their mixtures.

According to an advantageous embodiment of the invention, the alcohol is chosen from octyldodecanol.

non-aromatic, saturated or unsaturated, linear or branched mono- or diesters comprising up to 30 carbon atoms and advantageously from 12 to 30 carbon atoms and optionally comprising one or two ether groups.

Mention may be made, among the compounds of this type, of monoesters or diesters obtained from a saturated or unsaturated monocarboxylic or dicarboxylic fatty acid, in particular comprising from 4 to 28 and preferably from 4 to 24 carbon atoms, optionally comprising at least one free hydroxyl, on the one hand, and from a saturated or unsaturated monoalcohol or polyol, comprising from 2 to 26 and in particular from 3 to 24 carbon atoms and from 1 to 6 hydroxyl groups, on the other hand; the number of carbon atoms (excluding the carbonyl group) being at least 12 and preferably at least 16. In addition, the ester can optionally comprise one or two ether groups and can optionally comprise one or two hydroxyl groups.

Mention may be made, as examples of monoesters, of cetearyl octanoate, isononyl isononanoate, 2-ethylhexyl palmitate, 2-octyldodecyl neopentanoate, isopropyl myristate, isopropyl isostearate, isopropyl palmitate, butyl stearate, hexyl laurate, mixtures of esters of capric acid, of caprylic acid and of alcohol resulting from coconut ($C_{12}$-$C_{18}$ alcohols), 2-ethylhexyl palmitate, 2-hexadecyl laurate or their mixtures.

Mention may also be made of optionally hydroxylated monoesters or diesters of a $C_2$-$C_8$ mono- or polycarboxylic acid and of a $C_2$-$C_8$ alcohol. Suitable in particular for the implementation of the invention are the monoesters of a $C_2$-$C_8$ carboxylic acid and of a $C_2$-$C_8$ alcohol, which are optionally hydroxylated, and the diesters of a $C_2$-$C_8$ dicarboxylic acid and of a $C_2$-$C_8$ alcohol, which are optionally hydroxylated, such as diisopropyl adipate, di(2-ethylhexyl) adipate, dibutyl adipate or di(2-ethylhexyl) succinate.

Mention may also be made of esters of lanolic acid, of oleic acid, of lauric acid, of (iso)stearic acid or of ricinoleic acid and of diols, in particular glycols, such as propylene glycol monoisostearate or propylene glycol monoricinoleate.

Mention may be made, among suitable diesters, of di(2-ethylhexyl) succinate and diesters of glycol, in particular $C_2$-$C_5$ glycol, of glycerol or of diglycerol and of saturated or unsaturated and linear or branched monocarboxylic acids, such as neopentyl glycol dicaprate, neopentyl glycol diheptanoate, propylene glycol dioctanoate or diethylene glycol diisononanoate.

Use may also be made of hydroxylated monoesters and diesters, such as isostearyl lactate, octyl hydroxystearate or glyceryl stearate.

aromatic mono- or diesters comprising up to 30 carbon atoms and optionally comprising one or two ether groups.

Suitable are the monoesters of $C_{10}$-$C_{20}$ monoalcohols, more particularly $C_{12}$-$C_{15}$ alkyl benzoates.

Mention may also be made of the esters of a linear or branched, preferably saturated, in particular $C_2$-$C_{20}$, monoalcohol or polyol, optionally comprising two or three hydroxyl groups, and of benzoic acid.

Suitable as examples are the diesters of a saturated, linear or branched, $C_2$-$C_{10}$, more particularly $C_2$-$C_6$, polyol, comprising two or three hydroxyl groups, and of benzoic acid, preferably chosen from ethylene glycol dibenzoate, diethylene glycol dibenzoate, propylene glycol dibenzoate, dipropylene glycol dibenzoate and their mixtures.

non-aromatic, saturated or unsaturated, linear or branched triesters comprising less than 60 carbon atoms and optionally comprising one to three ether groups.

Suitable for the invention are the esters obtained from saturated or unsaturated, linear or branched, $C_2$-$C_{40}$, preferably $C_4$-$C_{40}$, mono- or polycarboxylic acids, which are optionally hydroxylated, and from $C_2$-$C_{40}$, preferably $C_3$-$C_{40}$, polyols or monoalcohols, the said polyester optionally comprising at least one free hydroxyl.

Use may be made, for example, of triacetin and also triglycerides of saturated or unsaturated $C_8$-$C_{20}$ fatty acids, such as, for example, triglycerides of heptanoic acid or octanoic acid; in particular, mention may be made of saturated triglycerides, such as caprylic/capric triglyceride, and their mixtures, for example such as that sold under the reference Myritol 318 of Cognis, glyceryl triheptanoate, glyceryl trioctanoate, triglycerides of $C_{18-36}$ acid, such as those sold under the reference DUB TGI 24 by Stéarineries Dubois), or glyceryl triisostearate.

Mention may also be made, by way of example, of oils comprising three ester functional groups, which are optionally hydroxylated or acetylated, of a $C_2$-$C_8$ acid comprising three carboxyl functional groups, which is optionally hydroxylated, and of a $C_2$-$C_8$, advantageously $C_2$-$C_4$, monoalcohol. Thus, mention may be made to citric acid esters, such as, for example, triethyl citrate, trioctyl citrate, tributyl citrate, tributyl acetylcitrate and their mixtures.

vegetable oils

Mention may be made, inter alia, of hydrocarbon vegetable oils, such as, for example, jojoba oil, unsaturated triglycerides, such as castor oil, olive oil, ximenia oil, pracaxi oil, coriander oil, macadamia oil, passionflower oil, argan oil, sesame seed oil, grape seed oil, avocado oil, apricot kernel oil (*Prunus armeniaca* kernel oil), the liquid fraction of shea butter, the liquid fraction of cocoa butter, and their mixtures their mixtures.

Preferably, the non-volatile hydrocarbon first oil is chosen from $C_{10}$-$C_{26}$ alcohols, more particularly monoalcohols, and preferably octyldodecanol.

The content of non-volatile polar hydrocarbon first oil(s) advantageously represents from 20% to 60% by weight and preferably from 25% to 55% by weight, with respect to the weight of the composition.

More particularly, when the composition comprises at least one wax, the content of non-volatile polar hydrocarbon first oil(s) advantageously represents from 20% to 55% by weight and preferably from 22% to 50% by weight, with respect to the weight of the composition.

According to an advantageous embodiment of the invention, the (alkylcellulose/alkylcellulose+first oil(s))*100 ratio by weight varies from 10% to 60%. Preferably, the said ratio by weight varies from 10% to 50%.

Optional Third Non-Volatile Oils

The present invention can optionally comprise at least one non-volatile hydrocarbon or silicone third oil different from the second oil or oils.

The third oil or oils are chosen so that it/they is/are compatible with the first oil or oils described above, according to the protocol described in detail previously.

The third oil or oils can be chosen from the abovementioned first oils insofar as it/they is/are compatible with the silicone or fluorinated second oil or oils, which will be described later, this characteristic being confirmed, in a simple way, by carrying out the protocol described previously.

They can also be chosen from non-volatile polar hydrocarbon oils different from the first oils, from non-polar hydrocarbon oils, from phenylated silicone oils not having a dimethicone fragment, and their mixtures.

Non-Volatile Polar Hydrocarbon Oils

Mention may be made, among the non-volatile hydrocarbon oils different from the non-volatile hydrocarbon first oils described above, of oils comprising at least one ester group, optionally at least one free hydroxyl group, more particularly chosen from non-aromatic, saturated or unsaturated, linear or branched mono- or diesters comprising more than 30 carbon atoms and optionally comprising one or two ether groups; non-aromatic, saturated or unsaturated, linear or branched triesters comprising at least 60 carbon atoms and optionally comprising one to three ether groups, and also their mixtures; aromatic mono- or diesters comprising up to 30 carbon atoms and optionally comprising one or two ether groups; tetraesters; polyesters obtained by condensation of unsaturated fatty acid dimer and/or trimer and of diol; esters and polyesters of diol dimer and of mono- or dicarboxylic acid; polyesters resulting from the esterification of at least one hydroxylated carboxylic acid triglyceride by an aliphatic monocarboxylic acid and by an aliphatic dicarboxylic acid, which is optionally unsaturated, and also their mixtures.

non-aromatic, saturated or unsaturated, linear or branched mono- or diesters comprising more than 30 carbon atoms and optionally comprising one or two ether groups.

Mention may be made, as examples of monoesters, of 2-octyldodecyl stearate, 2-octyldodecyl erucate, oleyl erucate, isostearyl isostearate, 2-octyldecyl palmitate, 2-octyldodecyl myristate or their mixtures.

Mention may be made, among suitable diesters, of isocetyl stearoyl stearate, diisostearyl adipate, diesters of glycol, in particular $C_2$-$C_5$ glycol, of glycerol or of diglycerol and of saturated or unsaturated and linear or branched monocarboxylic acids, such as polyglyceryl-2 diisostearate (in particular such as the compound sold under the commercial reference Dermol DGDIS by Alzo).

Use may also be made of hydroxylated monoesters and diesters, such as polyglyceryl-3 diisostearate, octyldodecyl hydroxystearate or diisostearyl malate.

non-aromatic, waturated or unsaturated, linear or branched triesters comprising at least 60 carbon atoms and optionally comprising one to three ether groups, and also their mixtures Mention may be made of triesters of glycerol or polyglycerol and of monocarboxylic acids, such as polyglycerol-2 triisostearate or glyceryl tri(2-decyltetradecanoate).

Tetraesters comprising in particular from 35 to 70 carbon atoms, such as tetraesters of pentaerythritol or polyglycerol and of a monocarboxylic acid, for example such as pentaerythrityl tetrapelargonate, pentaerythrityl tetraisostearate, pentaerythrityl tetraisononanoate, polyglyceryl-2 tetraisostearate or pentaerythrityl tetra(2-decyltetradecanoate).

Polyesters obtained by condensation of unsaturated fatty acid dimer and/or trimer and of diol, such as those described in Patent Application FR 0 853 634, such as in particular dilinoleic acid and 1,4-butanediol. Mention may in particular be made on this account of the polymer sold by Biosynthis under the name Viscoplast 14436H (INCI name: dilinoleic acid/butanediol copolymer) or else copolymers of polyols and of diacid dimers, and their esters, such as Hailucent ISDA.

Esters and polyesters of diol dimer and of mono- or dicarboxylic acid, such as esters of diol dimer and of fatty acid and esters of diol dimer and of dicarboxylic acid dimer, in particular which can be obtained from a dicarboxylic acid dimer derived in particular from the dimerization of an unsaturated fatty acid, in particular an unsaturated $C_8$ to $C_{34}$, in particular $C_{12}$ to $C_{22}$, especially $C_{16}$ to $C_{20}$ and more particularly $C_{18}$ fatty acid, such as esters of dilinoleic diacids and of dilinoleic diol dimers, for example such as those sold by Nippon Fine Chemical under the trade names Lusplan DD-DA5® and DD-DA7®.

Polyesters resulting from the esterification of at least one hydroxylated carboxylic acid triglyceride by an aliphatic monocarboxylic acid and by an aliphatic dicarboxylic acid, which is optionally unsaturated, such as the succinic acid and isostearic acid castor oil sold under the reference Zenigloss by Zenitech.

Non-Volatile Non-Polar Hydrocarbon Oils

These oils can be of vegetable, mineral or synthetic origin.

"Non-polar oil" is understood to mean, within the meaning of the present invention, an oil chosen from hydrocarbons, that is to say from compounds comprising only carbon and hydrogen atoms.

Preferably, the non-volatile non-polar hydrocarbon oil can be chosen from linear or branched hydrocarbons of mineral or synthetic origin, such as, for example:

liquid paraffin,
squalane,
isoeicosane,
naphthalene oil,
hydrogenated or non-hydrogenated polybutenes, such as, for example, Indopol H-100, Indopol H-300 or Indopol H-1500 from Amoco,
polyisobutenes and hydrogenated polyisobutenes, such as, for example, Parleam® from Nippon Oil Fats, Panalane H-300 E from Amoco, Viseal 20000 from Synteal, Rewopal PIB 1000 from Witco or alternatively Parleam Lite from NOF Corporation,
decene/butene copolymers and polybutene/polyisobutene copolymers, in particular Indopol L-14,
polydecenes and hydrogenated polydecenes, such as, for example: Puresyn 10, Puresyn 150 or Puresyn 6 from ExxonMobil Chemical,
and their mixtures.

Non-Volatile Phenylated Silicone Oils not having a Dimethicone Fragment

"Silicone oil" is understood to mean an oil containing at least one silicon atom and in particular containing Si—O groups.

The term "phenylated" specifies that the said oil comprises, in its structure, at least one phenyl radical.

The term "dimethicone fragment" denotes a divalent siloxane group, the silicon atom of which carries two methyl radicals, this group not being located at an or at the ends of the molecule. It can be represented by the following formula: —(Si(CH$_3$)$_2$—O)—.

"Non-volatile" is understood to mean an oil, the vapour pressure of which at 25° C. and atmospheric pressure is non-zero and less than 0.02 mmHg (2.66 Pa) and better still less than $10^{-3}$ mmHg (0.13 Pa).

The silicone oils which can be used within the meaning of the invention advantageously have a weight-average molecular weight of less than or equal to 150 000 g/mol, preferably of less than or equal to 100 000 g/mol and better still less than or equal to 10 000 g/mol.

Preferably, the silicones do not comprise a $C_2$-$C_3$ alkylene oxide group or a glycerolated group.

Mention may be made, as non-volatile phenylated silicone first oil not having a dimethicone fragment which is suitable for the present invention, of the following oils, alone or as mixtures:

a) the phenylated silicone oils corresponding to the following formula (I):

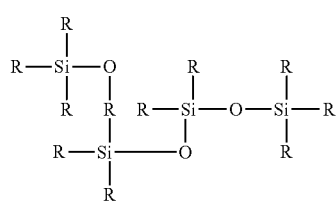

in which the R groups, which are monovalent or divalent, represent, independently of one another, a methyl or a phenyl, with the proviso that at least one R group represents a phenyl and that the formula (I) does not comprise a dimethicone fragment.

Preferably, in this formula, the phenyl silicone oil comprises at least three phenyl groups, for example at least four, at least five or at least six.

b) the phenylated silicone oils corresponding to the following formula (II):

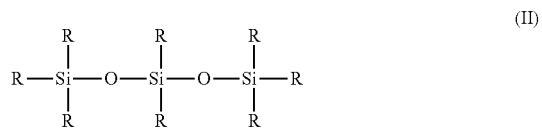

in which the R groups represent, independently of one another, a methyl or a phenyl, with the proviso that at least one R group represents a phenyl and that the formula (I) does not comprise a dimethicone fragment.

Preferably, in this formula, the compound of formula (II) comprises at least three phenyl groups, for example at least four or at least five.

Mixtures of different phenylorganopolysiloxane compounds described above can be used.

Examples which may be mentioned comprise mixtures of triphenyl-, tetraphenyl- or pentaphenylorganopolysiloxanes.

Mention may more particularly be made, among the compounds of formula (II), of phenylated silicone oils not having a dimethicone fragment, corresponding to the formula (II) in which at least 4 or at least 5 R radicals represent a phenyl radical, the remaining radicals representing methyls.

Such non-volatile phenylated silicone oils are preferably trimethylpentaphenyltrisiloxane or tetramethyltetraphenyltrisiloxane. They are in particular sold by Dow Corning under the reference PH-1555 HRI or Dow Corning 555 Cosmetic Fluid (chemical name: 1,3,5-trimethyl-1,1,3,5,5-pentaphenyltrisiloxane; INCI name: trimethylpentaphenyltrisiloxane), or the tetramethyltetraphenyltrisiloxane sold under the reference Dow Corning 554 Cosmetic Fluid by Dow Corning can also be used.

They correspond in particular to the following formulae (IIa) and (IIb):

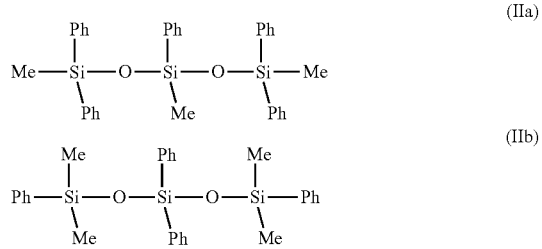

in which Me represents methyl, and Ph represents phenyl.

c) the phenylated silicone oils corresponding to the formula (III) below:

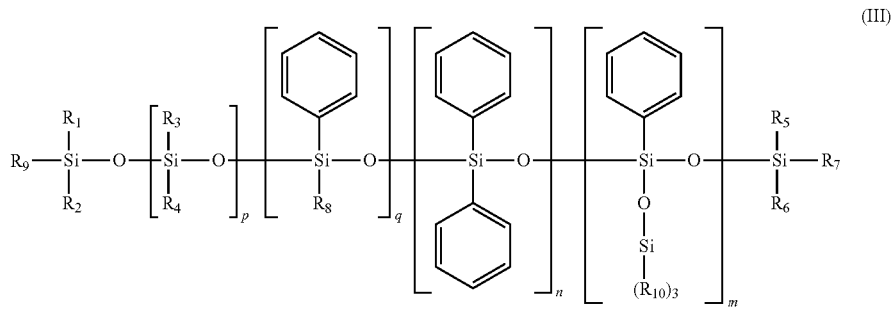

in which:

$R_1$ to $R_{10}$, independently of one another, are saturated or unsaturated and linear, cyclic or branched $C_1$-$C_{30}$ hydrocarbon radicals, m, n, p and q are, independently of one another, integers between 0 and 900, with the proviso that the sum m+n+q is other than 0 and that p is equal to 0 if $R_3$ and $R_4$ represent methyl groups.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$ represent, independently of one another, a saturated or unsaturated, preferably saturated, and linear or branched $C_1$-$C_{30}$ hydrocarbon radical, and in particular a preferably saturated $C_1$-$C_{20}$, in particular $C_1$-$C_{18}$, hydrocarbon radical, or a monocyclic or polycyclic $C_6$-$C_{14}$ and in particular $C_{10}$-$C_{13}$ aryl radical, or an aralkyl radical, the alkyl part of which is preferably a $C_1$-$C_3$ alkyl part.

Preferably, $R_1$ to $R_{10}$ can each represent a methyl, ethyl, propyl, butyl, isopropyl, decyl, dodecyl or octadecyl radical, or in an alternative form a phenyl, tolyl, benzyl or phenethyl radical. $R_1$ to $R_{10}$ can in particular be identical, and in addition can be a methyl radical.

According to a first more specific embodiment of the formula (III), mention may be made of:

i) the phenylated silicone oils corresponding to the formula (IIIi) below:

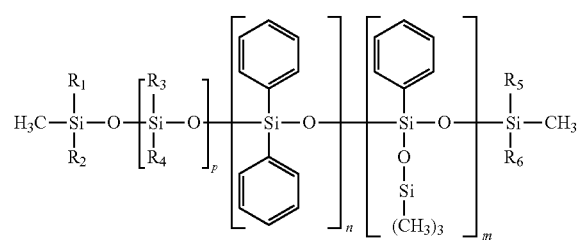

in which:

$R_1$ to $R_6$ are, independently of one another, saturated or unsaturated and linear, cyclic or branched $C_{01}$-$C_{30}$ hydrocarbon radicals, a preferably $C_6$-$C_{14}$ aryl radical or an aralkyl radical, the alkyl part of which is a $C_1$-$C_3$ alkyl part, m, n and p are, independently of one another, integers between 0 and 100, with the proviso that the sum n+m is between 1 and 100 and that p is equal to 0 if $R_3$ and $R_4$ represent methyl groups.

Preferably, $R_1$ to $R_6$ represent, independently of one another, a $C_1$-$C_{20}$, in particular $C_1$-$C_{18}$, hydrocarbon, preferably alkyl, radical, or a $C_6$-$C_{14}$ aryl radical which is monocyclic (preferably a $C_6$ aryl radical) or polycyclic and in particular a $C_{10}$-$C_{13}$ aryl radical, or an aralkyl radical (preferably the aryl part is a $C_6$ aryl part; the alkyl part is a $C_1$-$C_3$ alkyl part).

Preferably, $R_1$ to $R_6$ can each represent a methyl, ethyl, propyl, butyl, isopropyl, decyl, dodecyl or octadecyl radical, or in an alternative form a phenyl, tolyl, benzyl or phenethyl radical.

$R_1$ to $R_6$ can in particular be identical, and in addition can be a methyl radical. Preferably, m=1 or 2 or 3, and/or n=0 and p=0 can be applied, in the formula (IIIi).

According to a suitable alternative form, mention may be made of the compounds (B) deriving from the formula (IIIi) below:

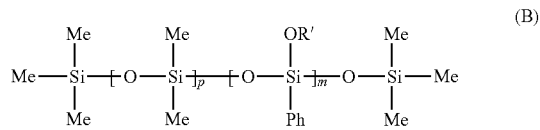

in which Me is methyl and Ph is phenyl, OR' represents an —OSiMe$_3$ group, p has the value 0 and m is between 1 and 1000. In particular, m and p are such that the compound (B) is a non-volatile oil.

Phenyltrimethylsiloxytrisiloxane, sold in particular under the reference Dow Corning 556 Cosmetic Grade Fluid by Dow Corning (INCI name: phenyl trimethicone), can be used, for example.

ii) the non-volatile phenylated silicone oils not having a dimethicone fragment corresponding to the formula (IIIii) below:

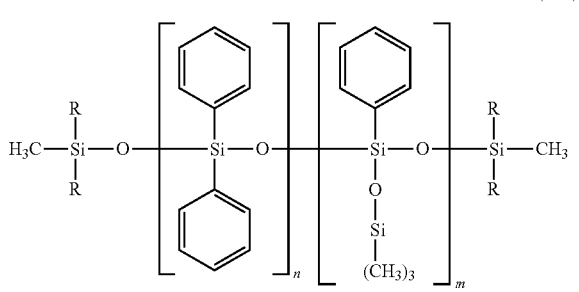

(IIIii)

in which:

R, independently of one another, are saturated or unsaturated and linear, cyclic or branched $C_1$-$C_{30}$ hydrocarbon radicals, preferably R is a $C_1$-$C_{30}$ alkyl radical, a preferably $C_6$-$C_{14}$ aryl radical, or an aralkyl radical, the alkyl part of which is a $C_1$-$C_3$ alkyl part, m and n are, independently of each other, integers between 0 and 100, with the proviso that the sum n+m is between 1 and 100.

Preferably, R represent, independently of one another, a saturated or unsaturated, preferably saturated, and linear or branched $C_1$-$C_{30}$ hydrocarbon radical, and in particular a preferably saturated $C_1$-$C_{20}$, in particular $C_1$-$C_{18}$ and more particularly $C_4$-$C_{10}$ hydrocarbon radical, a monocyclic or polycyclic $C_6$-$C_{14}$ and in particular $C_{10}$-$C_{13}$ aryl radical, or an aralkyl radical, of which preferably the aryl part is a $C_6$ aryl part and the alkyl part is a $C_1$-$C_3$ alkyl part.

Preferably, the R groups can each represent a methyl, ethyl, propyl, butyl, isopropyl, decyl, dodecyl or octadecyl radical, or in an alternative form a phenyl, tolyl, benzyl or phenethyl radical.

The R groups can in particular be identical, and in addition can be a methyl radical.

Preferably, m=1 or 2 or 3, and/or n=0 and/or p=0 or 1 can be applied, in the formula (IIIii).

According to a preferred embodiment, n is an integer between 0 and 100 and m is an integer between 1 and 100, with the proviso that the sum n+m is between 1 and 100, in the formula (IIIii). Preferably, R is a methyl radical.

According to one embodiment, a phenylated silicone oil of formula (IIIii) having a viscosity at 25° C. of between 5 and 1500 mm²/s (that is to say, from 5 to 1500 cSt) and preferably having a viscosity of between 5 and 1000 mm²/s (that is to say, from 5 to 1000 cSt) can be used. The values in brackets represent the viscosities at 25° C.

According to this embodiment, the non-volatile phenylated silicone oil is preferably chosen from phenyl trimethicones (when n=0), such as DC556 from Dow Corning, or else from diphenyl siloxy phenyl trimethicone oil (when m and n are between 1 and 100), such as KF-56A from Shin-Etsu, or the Silbione 70663V30 oil from Bluestar Silicones.

(d) the phenylated silicone oils corresponding to the following formula (IV):

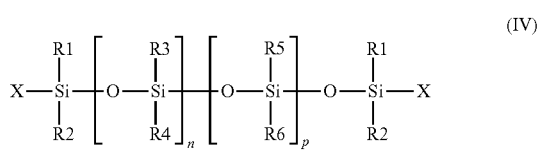

(IV)

in which:

$R_1$, $R_2$, $R_5$ and $R_6$, which are identical or different, are an alkyl radical containing from 1 to 6 carbon atoms, $R_5$ and $R_6$ not simultaneously representing a methyl radical, $R_3$ and $R_4$, which are identical or different, are an alkyl radical containing from 1 to 6 carbon atoms or an aryl radical (preferably a $C_6$-$C_{14}$ aryl radical), with the proviso that at least one of $R_3$ and $R_4$ is a phenyl radical, X is an alkyl radical containing from 1 to 6 carbon atoms, a hydroxyl radical or a vinyl radical, n and p being an integer greater than or equal to 1, chosen so as to confer, on the oil, a weight-average molecular weight of less than 150 000 g/mol and more preferably of less than 100 000 g/mol.

Preferably, the oil is chosen from the oils of formula (II) or (III), and and also their mixtures, and more preferably still from the phenyl silicone oils of formulae (IIa), (IIIi), in particular the formula (B), and (IIIii), and also their mixtures.

Especially, the oil may be chosen from trimethylpentaphenyltrisiloxane, phenyl trimethicone, diphenyl siloxy phenyl trimethicone, and their mixtures.

If the composition comprises at least one non-volatile third oil, the content of third oil(s) is between 4% and 40% by weight, with respect to the weight of the composition, and preferably between 10% and 30% by weight, with respect to the weight of the composition.

In the case of a composition comprising at least one wax, if this composition comprises at least one non-volatile third oil, then the content of third oil(s) is between 5% and 40% by weight, with respect to the weight of the composition, and preferably between 10% and 30% by weight, with respect to the weight of the composition.

Second Incompatible Non-Volatile Silicone or Fluorinated Oils(s)

As indicated above, the composition according to the invention comprises at least one non-volatile silicone or fluorinated second oil which is incompatible with the above-mentioned non-volatile polar hydrocarbon first oils.

The incompatibility of the non-volatile silicone or fluorinated second oil or oils is evaluated according to the protocol described above. In addition, this or these oils are employed at a content where they are incompatible with the non-volatile polar hydrocarbon first oil or oils.

"Non-volatile" is understood to mean an oil, the vapour pressure of which at 25° C. and atmospheric pressure is non-zero and less than 0.02 mmHg (2.66 Pa) and better still less than $10^{-3}$ mmHg (0.13 Pa).

More particularly, the incompatible non-volatile silicone second oil(s) are chosen from non-phenylated silicone oils or from non-volatile phenylated silicone oils having at least one dimethicone ($-$Si(CH$_3$)$_2$$-$O$-$) fragment.

The silicone oils which can be used within the meaning of the invention advantageously have a weight-average molecular weight of less than or equal to 150 000 g/mol, preferably of less than or equal to 100 000 g/mol and better still of less than or equal to 10 000 g/mol.

Preferably, the silicones do not comprise a $C_2$-$C_3$ alkylene oxide group or a glycerolated group.

Non-Volatile Phenylated Silicones Having at Least One Dimethicone Fragment

Mention may be made, as non-volatile phenylated silicone second oil having at least one dimethicone fragment which is suitable for use in the present invention, of the following oils, alone or as mixtures:

a) the phenylated silicone oils corresponding to the following formula (I'):

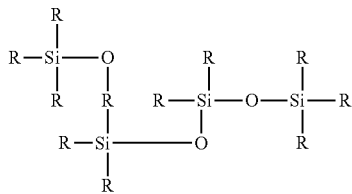
(I')

in which the R groups, which are monovalent or divalent, represent, independently of one another, a methyl or a phenyl, with the proviso that at least one R group represents a phenyl and that the formula (I') comprises at least one dimethicone fragment.

b) the phenylated silicone oils corresponding to the following formula (II'):

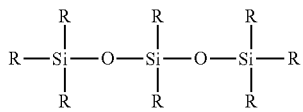
(II')

in which the R groups represent, independently of one another, a methyl or a phenyl, with the proviso that at least one R group represents a phenyl and that the formula (II') comprises at least one dimethicone fragment.

c) the phenylated silicone oils corresponding to the following formula (III'):

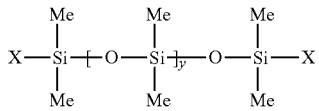
(III')

in which Me represents methyl, y is between 1 and 1000 and X represents —$CH_2$—$CH(CH_3)(Ph)$.

d) the phenylated silicone oils corresponding to the formula (IV') below:

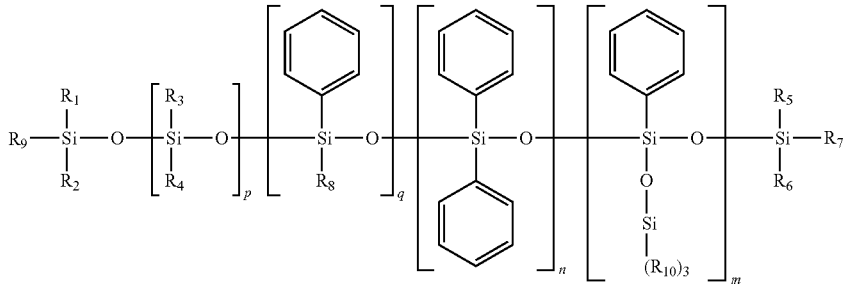
(IV')

in which:

$R_1$ to $R_{10}$, independently of one another, are saturated or unsaturated and linear, cyclic or branched $C_1$-$C_{30}$ hydrocarbon radicals, m, n, p and q are, independently of one another, integers between 0 and 900, with the proviso that the sum m+n+q is other than 0;

the formula (IV') comprising at least one dimethicone fragment.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$ represent, independently of one another, a saturated or unsaturated, preferably saturated, and linear or branched $C_1$-$C_{30}$ hydrocarbon radical, and in particular a preferably saturated $C_1$-$C_{20}$, in particular $C_1$-$C_{18}$, hydrocarbon radical, or a monocyclic or polycyclic $C_6$-$C_{14}$ and in particular $C_{10}$-$C_{13}$ aryl radical, or an aralkyl radical, the alkyl part of which is preferably a $C_1$-$C_3$ alkyl part.

Preferably, $R_1$ to $R_{10}$ can each represent a methyl, ethyl, propyl, butyl, isopropyl, decyl, dodecyl or octadecyl radical, or in an alternative form a phenyl, tolyl, benzyl or phenethyl radical. $R_1$ to $R_{10}$ can in particular be identical, and in addition can be a methyl radical.

According to a more specific embodiment of the formula (IV'), mention may be made of the phenylated silicone oils corresponding to the formula (IV'i) below:

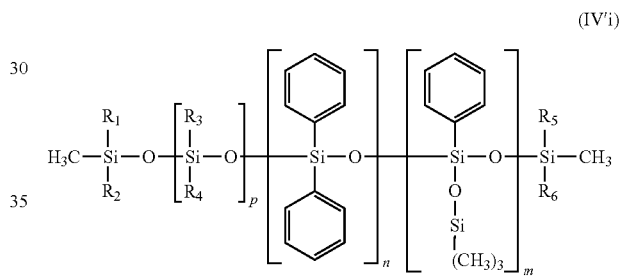
(IV'i)

in which:

$R_1$ to $R_6$ are, independently of one another, saturated or unsaturated and linear, cyclic or branched $C_1$-$C_{30}$ hydrocarbon radicals, a preferably $C_6$-$C_{14}$ aryl radical or an aralkyl radical, the alkyl part of which is a $C_1$-$C_3$ alkyl part, m, n and p are, independently of one another, integers between 0 and 100, with the proviso that the sum n+m is between 1 and 100, the formula (IV'i) comprising at least one dimethicone fragment.

Preferably, $R_1$ to $R_6$ represent, independently of one another, a $C_1$-$C_{20}$, in particular $C_1$-$C_{18}$, hydrocarbon, preferably alkyl, radical, or a $C_6$-$C_{14}$ aryl radical which is monocyclic (preferably a $C_6$ aryl radical) or polycyclic and in particular a $C_{10}$-$C_{13}$ aryl radical, or an aralkyl radical (preferably the aryl part is a $C_6$ aryl part; the alkyl part is a $C_1$-$C_3$ alkyl part); the formula (IV'i) comprising at least one dimethicone fragment.

Preferably, $R_1$ to $R_6$ can each represent a methyl, ethyl, propyl, butyl, isopropyl, decyl, dodecyl or octadecyl radical, or in an alternative form a phenyl, tolyl, benzyl or phenethyl radical; the formula (IV'i) comprising at least one dimethicone fragment.

$R_1$ to $R_6$ can in particular be identical, and in addition can be a methyl radical. Preferably, m=1 or 2 or 3, and/or n=0 and/or p=0 or 1 can be applied, in the formula (IV'i).

Preferably, the phenylated silicone oils which can be used as second oil in the context of the invention correspond to compounds of formula (IV'i) in which:

A) m=0 and n and p are, independently of each other, integers between 1 and 100.

Preferably, $R_1$ to $R_6$ are methyl radicals.

According to this embodiment, the silicone oil is preferably chosen from a diphenyl dimethicone, such as KF-54 from Shin-Etsu (400 cSt), KF-54HV from Shin-Etsu (5000 cSt), KF-50-300CS from Shin-Etsu (300 cSt), KF-53 from Shin-Etsu (175 cSt) or KF-50-100CS from Shin-Etsu (100 cSt).

B) p is between 1 and 100, the sum n+m is between 1 and 100, and n=0.

These phenylated silicone oils having or not having at least one dimethicone fragment correspond more particularly to the formula (B) below:

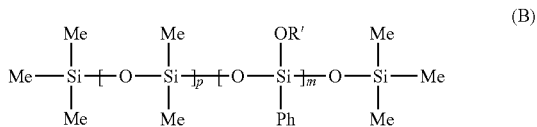

in which Me is methyl and Ph is phenyl, OR' represents an —OSiMe$_3$ group, p is between 1 and 1000 and m is between 1 and 1000. In particular, m and p are such that the compound (B) is a non-volatile oil.

According to a specific embodiment, the non-volatile phenylated silicone oil is such that p is between 1 and 1000, m being more particularly such that the compound (B) is a non-volatile oil. Use may be made, for example, of trimethylsiloxyphenyl dimethicone, sold in particular under the reference Belsil PDM 1000 by Wacker.

(e) the phenylated silicone oils corresponding to the following formula (V'):

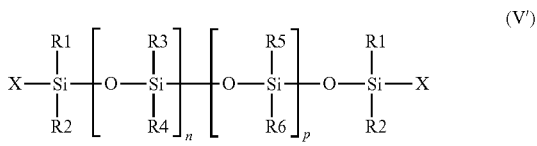

in which:

$R_1$, $R_2$, $R_5$ and $R_6$, which are identical or different, are an alkyl radical containing from 1 to 6 carbon atoms, $R_3$ and $R_4$, which are identical or different, are an alkyl radical containing from 1 to 6 carbon atoms or an aryl radical (preferably a $C_6$-$C_{14}$ aryl radical), with the proviso that at least one of $R_3$ and $R_4$ is a phenyl radical, X is an alkyl radical containing from 1 to 6 carbon atoms, a hydroxyl radical or a vinyl radical, n and p being an integer greater than or equal to 1, chosen so as to confer, on the oil, a weight-average molecular weight of less than 150 000 g/mol and more preferably of less than 100 000 g/mol;

the formula (V') comprising at least one dimethicone fragment.

Preferably, the second oil is chosen from the oils of formula (IV'), more particularly of formula (IV'i), and preferably the oils in accordance with the alternative forms (A) and (B), and also their mixtures.

Especially, the second oil can be chosen from diphenyl dimethicone, trimethylsiloxyphenyl dimethicone, and their mixtures.

Non-Volatile Non-Phenylated Silicone Oils

The expression "non-phenylated silicone oil" denotes a silicone oil not comprising phenyl substituents.

Representative examples of these non-volatile non-phenylated silicone oils which can be mentioned comprise polydimethylsiloxanes; alkyl dimethicones; vinyl methyl methicones; and also silicones modified with aliphatic groups and/or with functional groups, such as hydroxyl, thiol and/or amine groups, preferably hydroxyl groups.

It should be noted that "dimethicone" (INCI name) corresponds to a polydimethylsiloxane (chemical name).

The non-volatile non-phenylated silicone oil is preferably chosen from non-volatile dimethicone oils.

In particular, these oils can be chosen from the following non-volatile oils:

polydimethylsiloxanes (PDMSs),

PDMSs comprising aliphatic groups, in particular alkyl (or alkyl dimethicone) or alkoxy groups, which are pendent and/or at the end of the silicone chain, these groups each comprising from 2 to 24 carbon atoms. Mention may be made, by way of example, of cetyl dimethicone, sold under the commercial reference Abil Wax 9801 from Evonik Goldschmidt, PDMSs or alkyl dimethicones comprising functional groups, such as hydroxyl, thiol and/or amine groups, preferably hydroxyl groups, polysiloxanes modified with fatty acids or fatty alcohols, and their mixtures.

Preferably, these non-volatile non-phenylated silicone oils are chosen from polydimethylsiloxanes; alkyl dimethicones comprising $C_2$-$C_{24}$ alkyl groups, these silicone oils optionally comprising functional groups, such as hydroxyl, thiol and/or amine groups, preferably hydroxyl groups; and also their mixtures.

The non-volatile non-phenylated silicone oil can be chosen in particular from silicones of formula (I):

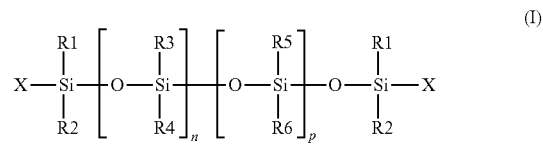

in which:

$R_1$, $R_2$, $R_5$ and $R_6$ are, together or separately, an alkyl radical containing from 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, the viscosity of which at 25° C. is in particular between 8 centistokes (cSt) ($8 \times 10^{-6}$ m$^2$/s) and 800 000 cSt, and a weight-average molecular weight of less than or equal to 150 000 g/mol, preferably of less than or equal to 100 000 g/mol and better still of less than or equal to 10 000 g/mol.

There may be mentioned, as non-volatile non-phenylated silicone oils suitable for the implementation of the invention, those for which:

the $R_1$ to $R_6$ and X substituents represent a methyl group, and p and n are such that the viscosity is 60 000 cSt, for example the product sold under the name Dow Corning 200 Fluid 60 000 CS by Dow Corning and the product sold under the name Wacker Belsil DM 60 000 by Wacker, the $R_1$ to $R_6$ and X substituents represent a methyl group, and p and n are such that the viscosity is 100 cSt or 350 cSt, for example the products sold respectively under the names Belsil DM100 and Dow Corning 200 Fluid 350 CS by Dow Corning, and the $R_1$ to $R_6$ substituents represent a methyl group, the X group represents a hydroxyl group, and n and p are such that the viscosity is 700 cSt, for example the product sold under the name Baysilone Fluid T0.7 by Momentive.

Non-Volatile Fluorinated Oils

The composition according to the invention can comprise, as second oil, at least one non-volatile fluorinated oil.

"Fluorinated oil" is understood to mean an oil containing at least one fluorine atom.

Mention may be made, as examples of fluorinated oils, of fluorosilicone oils, fluorinated polyethers, fluorinated silicones, in particular as described in the document EP-A-847 752, and perfluorinated compounds, alone or as mixtures.

Perfluorinated compounds is understood to mean, according to the invention, compounds in which all the hydrogen atoms have been replaced by fluorine atoms.

According to a preferred embodiment, the fluorinated oil is chosen from perfluorinated oils.

Mention may be made, as examples of perfluorinated oils, of perfluorodecalins, perfluoroperhydrophenanthrenes and perfluorinated ether oils.

According to a preferred embodiment, the fluorinated oil is chosen from perfluoroperhydrophenanthrenes and in particular the Fiflow® products sold by Creations Couleurs. In particular, use may be made of the fluorinated oil, the INCI name of which is perfluoroperhydrophenanthrene, sold under the reference Fiflow 220 by F2 Chemicals, or alternatively the perfluoropolymethylisopropyl ether oil sold, for example, under the reference Fomblin HC by Solvay.

Preferably, the second oil is chosen from silicone oils, and particularly from the oils of formula (IV'), preferably of formula (IV'i), with in particular the oils in accordance with the alternative forms (A) and (B), from polydimethylsiloxanes (PDMSs), and also their mixtures.

Especially, the second oil can be chosen from diphenyl dimethicone, trimethylsiloxyphenyl dimethicone, from polydimethylsiloxanes (PDMSs), and their combinations.

The content of non-volatile fluorinated or silicone second oil(s) is at least 20% by weight, preferably from 20% to 50% by weight and preferably from 25% to 45% by weight, with respect to the weight of the composition.

Additional Volatile Oils

According to a specific embodiment of the invention, the composition can also comprise at least one volatile oil.

The volatile oil can in particular be a silicone oil, a hydrocarbon oil, which is preferably non-polar, and also their mixtures.

"Volatile" is understood to mean an oil, the vapour pressure at 25° C. and atmospheric pressure of which is between 0.13 Pa and 40 000 Pa (0.001 and 300 mmHg) and preferably between 1.3 Pa and 1300 Pa (0.01 and 10 mmHg).

Mention may be made, as volatile silicone oils which can be used in the invention, of linear or cyclic silicones having a viscosity at ambient temperature of less than 8 centistokes (cSt) ($8 \times 10^{-6}$ m$^2$/s) and having in particular from 2 to 10 silicon atoms and especially from 2 to 7 silicon atoms, these silicones optionally comprising alkyl or alkoxy groups having from 1 to 10 carbon atoms.

Mention may in particular be made, as volatile silicone oils which can be used in the invention, of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and their mixtures.

Mention may be made, among volatile hydrocarbon oils, preferably volatile non-polar hydrocarbon oils, of volatile hydrocarbon oils having from 8 to 16 carbon atoms and their mixtures, and in particular:

branched $C_8$-$C_{16}$ alkanes, such as $C_8$-$C_{16}$ isoalkanes (also known as isoparaffins), isododecane, isodecane or isohexadecane, for example the oils sold under the Isopar or Permethyl trade name, linear alkanes, for example such as n-dodecane ($C_{12}$) and n-tetradecane ($C_{14}$), sold by Sasol respectively under the references Parafol 12-97 and Parafol 14-97, and also their mixtures, the undecane-tridecane mixture (Cetiol UT), the mixtures of n-undecane ($C_{11}$) and of n-tridecane ($C_{13}$) obtained in Examples 1 and 2 of Application WO 2008/155059 from Cognis, and their mixtures.

Preferably, if the composition comprises at least one volatile oil, the latter is chosen from volatile hydrocarbon oils.

When the composition comprises at least one additional volatile oil, their content more particularly represents from 5% to 30% by weight and more particularly from 10% to 20% by weight, with respect to the total weight of the said composition.

Waxes

As indicated above, the composition according to the invention can comprise at least one wax.

"Wax" is understood to mean, within the meaning of the present invention, a lipophilic compound which is solid at ambient temperature (25° C.), which exhibits a reversible solid/liquid change in state and which has a melting point of greater than or equal to 30° C. which can range up to 120° C.

The melting point of the wax can be measured using a differential scanning calorimeter (DSC), for example the calorimeter sold under the name DSC 30 by Mettler, or the calorimeter sold under the name DSC Q100 by TA Instruments with the software "TA Universal Analysis".

Preferably, the measuring protocol is as follows:

A sample of 5 mg of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The wax can in particular exhibit a hardness ranging from 0.05 MPa to 15 MPa and preferably ranging from 6 MPa to 15 MPa. The hardness is determined by measuring the compressive force, measured at 20° C. using the texture analyser sold under the name TA-TX2i by Rheo, equipped with a stainless-steel cylinder with a diameter of 2 mm, travelling at a measuring speed of 0.1 mm/second and penetrating the wax to a penetration depth of 0.3 mm.

The waxes can be hydrocarbon or fluorinated waxes and can be of vegetable, mineral, animal and/or synthetic origin.

In particular, the waxes exhibit a melting point of greater than 30° C. and better still of greater than 45° C.

Non-Polar Wax "Non polar wax" is understood to mean, within the meaning of the present invention, a wax for which the solubility parameter $\delta_a$ at 25° C. as defined below is equal to 0 $(J/cm^3)^{1/2}$.

The non-polar waxes are in particular hydrocarbon waxes formed solely of carbon and hydrogen atoms and devoid of heteroatoms, such as N, O, Si and P.

Mention may in particular be made, by way of illustration of the non-polar waxes suitable for the invention, of hydrocarbon waxes, for instance microcrystalline waxes, paraffin waxes, ozokerite, polymethylene waxes, polyethylene waxes and microwaxes, in particular of polyethylene.

Polar Wax "Polar wax" is understood to mean, within the meaning of the present invention, a wax for which the solubility parameter $\delta_a$ at 25° C. is other than 0 $(J/cm^3)^{1/2}$.

In particular, "polar wax" is understood to mean a wax, the chemical structure of which is formed essentially of, indeed even consists of, carbon and hydrogen atoms, and comprising at least one highly electronegative heteroatom, such as an oxygen, nitrogen, silicon or phosphorus atom.

The definition and calculation of the solubility parameters in the Hansen three-dimensional solubility space are described in the paper by C. M. Hansen: *The three-dimensional solubility parameters*, J. Paint Technol., 39, 105 (1967).

According to this Hansen space:

$\delta_D$ characterizes the London dispersion forces resulting from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the forces of specific interactions (such as hydrogen bonds, acid/base bonds, donor/acceptor bonds, and the like);

$\delta_a$ is determined by the equation: $\delta_a=(\delta_p^2+\delta_h^2)^{1/2}$.

The parameters $\delta_p$, $\delta_h$, $\delta_D$ and $\delta_a$ are expressed as $(J/cm^3)^{1/2}$.

The polar waxes can in particular be hydrocarbon, fluorinated or silicone waxes.

Preferably, the polar waxes can be hydrocarbon or silicone waxes.

"Silicone wax" is understood to mean an oil comprising at least one silicon atom and in particular comprising Si—O groups.

"Hydrocarbon wax" is understood to mean a wax formed essentially of, indeed even consisting of, carbon and hydrogen atoms, and optionally of oxygen and nitrogen atoms, and which does not contain a silicon or fluorine atom. It can contain alcohol, ester, ether, carboxylic acid, amine and/or amide groups.

According to a first preferred embodiment, the polar wax is a hydrocarbon wax.

Preference is in particular given, as polar hydrocarbon wax, to a wax chosen from ester waxes and alcohol waxes.

"Ester wax" is understood to mean, according to the invention, a wax comprising at least one ester functional group. The ester waxes can in addition be hydroxylated.

"Alcohol wax" is understood to mean, according to the invention, a wax comprising at least one alcohol functional group, that is to say comprising at least one free hydroxyl (OH) group.

Mention may be made, as silicone wax, for example, of the mixtures comprising a compound of C30-45 Alkyldimethylsilyl Polypropylsilsesquioxane (INCI name) type, for example the product Dow Corning SW-8005 C30 Resin Wax sold by Dow Corning. Mention may also made of the mixtures comprising a compound of the C30-45 Alkyl Methicone (INCI name) type, such as, for example, the product Dow Corning® AMS-C30 Cosmetic Wax. Mention may also be made of siliconized beeswax.

Use may in particular be made, as ester wax, of:

ester waxes, such as those chosen from:

i) waxes of formula $R_1COOR_2$, in which $R_1$ and $R_2$ represent linear, branched or cyclic aliphatic chains, the number of atoms of which varies from 10 to 50 and which can contain a heteroatom, such as O, N or P, and the melting point temperature of which varies from 25 to 120° C. In particular, use may be made, as ester wax, of a $C_{20}$-$C_{40}$ alkyl (hydroxystearyloxy)stearate (the alkyl group comprising from 20 to 40 carbon atoms), alone or as a mixture, or a $C_{20}$-$C_{40}$ alkyl stearate. Such waxes are sold in particular under the names Kester Wax K 82 P®, Hydroxypolyester K 82 P®, Kester Wax K 80 P® or Kester Wax K82H by Koster Keunen.

Use may also be made of a glycol and butylene glycol montanate (octacosanoate), such as the wax Licowax KPS Flakes (INCI name: glycol montanate) sold by Clariant.

ii) di(1,1,1-trimethylolpropane) tetrastearate, sold under the name Hest 2T-4S® by Heterene.

iii) diester waxes of a dicarboxylic acid of general formula $R^3$—(—OCO—$R^4$—COO—$R^5$), in which $R^3$ and $R^5$ are identical or different, preferably identical, and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturations. Preferably, the $C_4$-$C_{30}$ aliphatic group is linear and unsaturated.

iv) Mention may also be made of the waxes obtained by catalytic hydrogenation of animal or vegetable oils having in particular linear or branched $C_8$-$C_{32}$ fatty chains, for example such as hydrogenated jojoba oil, hydrogenated sunflower oil, hydrogenated castor oil or hydrogenated coconut oil, and also the waxes obtained by hydrogenation of castor oil esterified with cetyl alcohol, such as those sold under the names Phytowax Ricin 16L64® and 22L73® by Sophim. Such waxes are described in Application FR-A-2 792 190. Mention may be made, as waxes obtained by hydrogenation of olive oil esterified with stearyl alcohol, of that sold under the name Phytowax Olive 18 L 57.

v) Mention may also be made of waxes of animal or vegetable origin, such as beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumac wax, montan wax, orange wax, laurel wax, hydrogenated jojoba wax or sunflower wax, in particular refined sunflower wax.

According to another embodiment, the polar wax can be an alcohol wax.

Mention may be made, as alcohol wax, of mixtures of saturated linear $C_{30}$-$C_{50}$ alcohols, such as, for example, the wax Performacol 550 Alcohol from New Phase Technology, stearyl alcohol and cetyl alcohol.

Preferably, if the composition comprises it, the wax is chosen from non-polar hydrocarbon waxes; polar hydrocarbon waxes, such as waxes of animal or vegetable origin obtained or not obtained by catalytic hydrogenation of animal or vegetable oils; alcohol waxes; and also their mixtures.

The wax content advantageously varies from 0.5% to 20% by weight, in particular from 1% to 15% by weight and preferably from 5% to 12% by weight, with respect to the weight of the composition.

Pasty Compounds

The composition according to the invention can also comprise at least one compound which is pasty at ambient temperature and atmospheric pressure.

It should be noted that this pasty compound is water-immiscible. The protocol described in detail previously for the oils is valid in the case of a pasty compound in so far as the measurement takes place at a temperature at which the said pasty compound is in the liquid form.

"Pasty" is understood to mean, within the meaning of the present invention, a compound exhibiting a reversible solid/liquid change in state, having an anisotropic crystal organization in the solid state and comprising, at a temperature of 23° C., a liquid fraction and a solid fraction.

In other words, the starting melting point of the pasty compound can be less than 23° C. The liquid fraction of the pasty compound, measured at 23° C., can represent from 9% to 97% by weight of the pasty compound. This liquid fraction at 23° C. preferably represents between 15% and 85% and more preferably between 40% and 85% by weight.

Within the meaning of the invention, the melting point corresponds to the temperature of the most endothermic peak observed in thermal analysis (DSC) as described in Standard ISO 11357-3: 1999. The melting point of a pasty compound can be measured using a differential scanning calorimeter (DSC), for example the calorimeter sold under the name MDSC 2920 by TA Instruments, or the calorimeter sold under the name DSC Q100 by TA Instruments with the software "TA Universal Analysis".

The measurement protocol is as follows:

A sample of 5 mg of pasty compound placed in a crucible is subjected to a first temperature rise passing from −20° C. to 100° C., at a heating rate of 10° C./minute, is then cooled from 100° C. to −20° C. at a cooling rate of 10° C./minute and is finally subjected to a second temperature rise passing from −20° C. to 100° C. at a heating rate of 5° C./minute. During the second temperature rise, the variation in the difference in power absorbed by the empty crucible and by the crucible containing the sample of pasty fatty substance is measured as a function of the temperature. The melting point of the pasty compound is the temperature value corresponding to the tip of the peak of the curve representing the variation in the difference in power absorbed as a function of the temperature.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the latter in order to change from the solid state to the liquid state. The pasty compound is said to be in the solid state when all of its mass is in the crystalline solid form. The pasty compound is said to be in the liquid state when all of its mass is in the liquid form.

The enthalpy of fusion of the pasty compound is equal to the area under the curve of the thermogram obtained using a differential scanning calorimeter (DSC), such as the calorimeter sold under the name MDSC 2920 by TA Instruments, with a temperature rise of 5° C. or 10° C. per minute, according to Standard ISO 11357-3; 1999.

The enthalpy of fusion of the pasty compound is the amount of energy necessary to make the pasty compound change from the solid state to the liquid state. It is expressed in J/g.

The enthalpy of fusion consumed at 23° C. is the amount of energy absorbed by the sample to change from the solid state to the state which it exhibits at 23° C., consisting of a liquid fraction and a solid fraction.

The liquid fraction of the pasty compound measured at 32° C. preferably represents from 30% to 100% by weight of the pasty compound, preferably from 50% to 100% and more preferably from 60% to 100% by weight of the pasty compound. When the liquid fraction of the pasty compound, measured at 32° C., is equal to 100%, the temperature of the end of the melting range of the pasty compound is less than or equal to 32° C.

The liquid fraction of the pasty compound, measured at 32° C., is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound can in particular be chosen from synthetic pasty compounds and fatty substances of vegetable origin.

The pasty compound or compounds can be chosen in particular from:

lanolin and its derivatives, such as lanolin alcohol, oxyethylenated lanolins, acetylated lanolin, lanolin esters, such as isopropyl lanolate, or oxypropylenated lanolins;

petroleum jelly (also known as petrolatum);

polyol ethers chosen from poly($C_2$-$C_4$ alkylene) glycol pentaerythrityl ethers, fatty alcohol ethers of sugars, and their mixtures. For example, mention may be made of polyethylene glycol pentaerythrityl ether comprising 5 oxyethylene units (5 OE) (CTFA name: PEG-5 Pentaerythrityl Ether), polypropylene glycol pentaerythrityl ether comprising 5 oxypropylene (5 OP) units (CTFA name: PPG-5 Pentaerythrityl Ether), and their mixtures, and more especially the PEG-5 Pentaerythrityl Ether, PPG-5 Pentaerythrityl Ether and soybean oil mixture sold under the Lanolide name by Vevy, which is a mixture in which the constituents are in a 46/46/8 ratio by weight: 46% PPG-5 pentaerythrityl ether, 46% PPG-5 pentaerythrityl ether and 8% soybean oil, polymeric or non-polymeric silicone compounds, polymeric or non-polymeric fluorinated compounds, vinyl polymers, in particular:

olefin homopolymers and copolymers, hydrogenated diene homopolymers and copolymers, linear or branched homo- or copolymer oligomers of alkyl (meth)acrylates preferably having a $C_8$-$C_{30}$ alkyl group, homo- and copolymer oligomers of vinyl esters having $C_8$-$C_{30}$ alkyl groups, and homo- and copolymer oligomers of vinyl ethers having $C_8$-$C_{30}$ alkyl groups, liposoluble polyethers resulting from the polyetherification between one or more $C_2$-$C_{100}$ and preferably $C_2$-$C_{50}$ diols.

Consideration is given in particular, among the liposoluble polyethers, to copolymers of ethylene oxide and/or of propylene oxide with long-chain $C_6$-$C_{30}$ alkylene oxides, more preferably such that the ratio by weight of the ethylene oxide and/or propylene oxide to alkylene oxides in the copolymer is from 5:95 to 70:30. In this family, mention will be made in particular of copolymers such that the long-chain alkylene oxides are arranged in blocks having an average molecular weight from 1000 to 10 000, for example a polyoxyethylene/polydodecyl glycol block copolymer, such as the ethers of dodecanediol (22 mol) and of polyethylene glycol (45 OE) sold under the brand name Elfacos ST9 by Akzo Nobel.

esters and polyesters.

Consideration is given in particular, among the esters, to:

esters of a glycerol oligomer, in particular diglycerol esters, especially condensates of adipic acid and of diglycerol, for which a portion of the hydroxyl groups of the glycerols have reacted with a mixture of fatty acids, such as stearic acid, capric acid, isostearic acid and 12-hydroxystearic acid, such as, for example, bis-diglyceryl polyacyladipate-2, sold under the reference Softisan® 649 by Cremer Oleo, vinyl ester homopolymers having $C_8$-$C_{30}$ alkyl groups, such as polyvinyl laurate (sold in particular under the reference Mexomer PP by Chimex), arachidyl propionate, sold under the trade name Waxenol 801 by Alzo, stearyl heptanoate/stearyl caprylate mixtures, such as, for example, the product Dub Solide sold by Stearinerie Dubois, phytosterol esters, fatty acid triglycerides and their derivatives, pentaerythritol esters, esters of diol dimer and of diacid dimer, if appropriate esterified on their free alcohol or acid functional group(s) with acid or alcohol radicals, in particular dimer dilinoleate esters; such esters can be chosen in particular from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool S) and their mixtures, butters of vegetable origin, such as mango butter, for example that sold under the reference Lipex 203 by AarhusKarlshamn, shea butter, in particular that for which the INCI name is Butyrospermum Parkii Butter, such as that sold under the reference Sheasoft® by AarhusKarlshamn, cupuacu butter (Rain Forest RF3410 from Beraca Sabara), murumuru butter (Rain Forest RF3710 from Beraca Sabara), cocoa butter; and also orange wax, such as, for example, that which is sold under the reference Orange Peel Wax by Koster Keunen, completely or partially hydrogenated vegetable oils, such as, for example, hydrogenated soybean oil, hydrogenated coconut oil, hydrogenated rapeseed oil, mixtures of hydrogenated vegetable oils, such as the mixture of hydrogenated soybean, coconut, palm and rapeseed vegetable oil, for example the mixture sold under the reference Akogel® by AarhusKarlshamn (INCI name Hydrogenated Vegetable Oil), the trans-isomerized partially hydrogenated jojoba oil manufactured or sold by Desert Whale under the commercial reference Iso-Jojoba-50®, partially hydrogenated olive oil, such as, for example, the compound sold under the reference Beurrolive by Soliance, hydrogenated castor oil esters, such as hydrogenated castor oil dimer dilinoleate, for example Risocast DA-L sold by Kokyu Alcohol Kogyo, or hydrogenated castor oil isostearate, for example Salacos HCIS (V-L) sold by Nisshin Oil, and their mixtures.

Preferably, the pasty compounds which are suitable for the implementation of the invention are chosen from hydrocarbon compounds and comprise, besides the carbon and hydrogen atoms, at least oxygen atoms. The pasty compounds thus do not comprise a silicon atom or a fluorine atom.

According to a preferred embodiment, the pasty compound is chosen from petroleum jelly, esters and their mixtures. In particular, the pasty compound or compounds are chosen from petroleum jelly, esters of glycerol oligomers, stearyl heptanoate/stearyl caprylate mixtures, butters of vegetable origin, completely or partially hydrogenated vegetable oils, hydrogenated castor oil esters, or their mixtures.

If the composition comprises at least one pasty compound, their content varies from 0.5% to 15% by weight and preferably from 2% to 12% by weight, with respect to the weight of the composition.

Colourng Substances

The composition according to the invention can advantageously comprise at least one colouring substance chosen from pigments or pearlescent agents.

"Pigments" should be understood as meaning white or coloured and inorganic (mineral) or organic particles which are insoluble in the lipophilic phase(s) and which are intended to colour and/or opacify the composition and/or the deposited layer produced with the composition.

The pigments may be chosen from mineral pigments, organic pigments and composite pigments (i.e. pigments based on mineral and/or organic materials).

The pigments can be chosen from mineral pigments, in particular monochromatic pigments, organic lakes, pearlescent agents and goniochromatic pigments.

If the composition comprises them, their content varies from 0.1% to 15% by weight, with respect to the weight of the composition, and preferably from 0.5% to 12% by weight, with respect to the weight of the composition.

The mineral pigments can be chosen from metal oxide pigments, chromium oxides, iron oxides (black, yellow, red), titanium dioxide, zinc oxides, cerium oxides, zirconium oxides, chromium hydrate, manganese violet, Prussian blue, ultramarine blue, ferric blue, metal powders, such as aluminium powders or copper powder, and their mixtures.

Organic Lakes are Organic Pigments Formed of a Dye Attached to a Substrate.

The lakes, which are also known as organic pigments, can be chosen from the materials below and their mixtures:

cochineal carmine;

organic pigments of azo dyes, anthraquinone dyes, indigoid dyes, xanthene dyes, pyrene dyes, quinoline dyes, triphenylmethane dyes or fluoran dyes.

Mention may in particular be made, among the organic pigments, of those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 or FD&C Yellow No. 6;

the organic lakes can be insoluble sodium, potassium, calcium, barium, aluminium, zirconium, strontium or titanium salts of acid dyes, such as azo, anthraquinone, indigoid, xanthene, pyrene, quinoline, triphenylmethane or fluoran dyes, these dyes possibly comprising at least one carboxylic or sulfonic acid group.

The organic lakes can also be supported by an organic support, such as rosin or aluminium benzoate, for example.

Mention may in particular be made, among the organic lakes, of those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake or FD&C Yellow No. 6 Aluminium lake.

Mention may also be made of liposoluble dyes, such as, for example, Sudan Red, DC Red 17, DC Green 6, β-carotene, soybean oil, Sudan Brown, DC Yellow 11, DC Violet 2, DC Orange 5 or quinoline yellow.

The chemical substances corresponding to each of the organic colourants cited above are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

The pigments may also have been subjected to a hydrophobic treatment.

The hydrophobic treatment agent can be chosen from silicones, such as methicones, dimethicones, alkoxysilanes and perfluoroalkylsilanes; fatty acids, such as stearic acid; metal soaps, such as aluminium dimyristate, the aluminium salt of hydrogenated tallow glutamate, perfluoroalkyl phosphates, perfluoroalkylsilanes, perfluoroalkylsilazanes, poly (hexafluoropropylene oxide)s, polyorganosiloxanes comprising perfluoroalkyl perfluoropolyether groups and amino acids; N-acylated amino acids or their salts; lecithin, isopropyl triisostearyl titanate, and their mixtures.

The N-acylated amino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be aluminium, magnesium, calcium, zirconium, zinc, sodium or potassium salts. The amino acid can, for example, be lysine, glutamic acid or alanine.

The term "alkyl" cited in the abovementioned compounds denotes in particular an alkyl group having from 1 to 30 carbon atoms and preferably having from 5 to 16 carbon atoms.

Hydrophobic treated pigments are described in particular in Application EP-A-1 086 683.

Pearlescent Agents

Within the meaning of the present patent application, "pearlescent agent" is understood to mean coloured particles of any shape, which are or are not iridescent, produced in particular by certain molluscs in their shells or else synthesized, and which exhibit a colour effect via optical interference.

Mention may be made, as examples of pearlescent agents, of pearlescent pigments, such as titanium oxide-coated mica covered with an iron oxide, mica covered with bismuth oxychloride, titanium oxide-coated mica covered with chromium oxide, titanium oxide-coated mica covered with an organic dye, in particular of the abovementioned type, and also pearlescent pigments based on bismuth oxychloride.

They can also be mica particles, at the surface of which are superimposed at least two successive layers of metal oxides and/or of organic colourants.

The pearlescent agents can more particularly have a yellow, pink, red, bronze, orangey, brown, gold and/or coppery colour or glint.

Mention may be made, by way of illustration of the pearlescent agents which can be introduced as interference pigment into the first composition, of gold-coloured pearlescent agents sold in particular by BASF under the name Brilliant Gold 212G (Timica), Gold 222C (Cloisonne), Sparkle Gold (Timica) and Monarch Gold 233X (Cloisonne); bronze pearlescent agents sold in particular by Merck under the names Bronze Fine (17384) (Colorona) and Bronze (17353) (Colorona) and by BASF under the name Super Bronze (Cloisonne); orange pearlescent agents sold in particular by BASF under the name Orange 363C (Cloisonne) and by Merck under the names Passion Orange (Colorona) and Matte Orange (17449) (Microna); brown-coloured pearlescent agents sold in particular by BASF under the names Nu-Antique Copper 340XB (Cloisonne) and Brown CL4509 (Chroma-lite); pearlescent agents with a copper glint sold in particular by BASF under the name Copper 340A (Timica); pearlescent agents with a red glint sold in particular by Merck under the name Sienna Fine (17386) (Colorona); pearlescent agents with a yellow glint sold in particular by BASF under the name Yellow (4502) (Chroma-lite); red-coloured pearlescent agents with a gold glint sold in particular by BASF under the name Sunstone G012 (Gemtone); pink pearlescent agents sold in particular by BASF under the name Tan Opal G005 (Gemtone); black pearlescent agents with a gold glint sold in particular by BASF under the name Nu-Antique Bronze 240 AB (Timica); blue pearlescent agents sold in particular by Merck under the name Matte Blue (17433) (Microna); white pearlescent agents with a silvery glint sold in particular by Merck under the name Xirona Silver; and golden green pinkish orangey pearlescent agents sold in particular by Merck under the name Indian Summer (Xirona); and their mixtures.

Goniochromatic Pigments "Goniochromatic pigment" denotes, within the meaning of the present invention, a pigment which makes it possible to obtain, when the composition is spread over a substrate, a colour distance in the a*b* plane of the CIE 1976 colourimetric space which corresponds to a variation Dh° in the angle of hue h° of at least 20° when the angle of observation is varied with respect to the normal by between 0° and 80°, for an angle of incidence of the light of 45°.

The colour distance can be measured, for example, using a spectrogonioreflectometer of the Instrument Systems brand and with the GON 360 Goniometer reference, after the composition has been spread in the fluid state with a thickness of 300 µm using an automatic spreader over a contrast chart of the Erichsen brand and with the Type 24/5 reference, the measurement being carried out on the black background of the chart.

The goniochromatic pigment can be chosen, for example, from multilayer interference structures and liquid crystal colouring agents.

In the case of a multilayer structure, the latter can comprise, for example, at least two layers, each layer being produced, for example, from at least one material chosen from the group consisting of the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers and their combinations.

The multilayer structure may or may not exhibit, with respect to a central layer, a symmetry with regard to the chemical nature of the stacked layers.

Different effects are obtained according to the thickness and the nature of the various layers.

Examples of symmetrical multilayer interference structures are, for example, the following structures: $Fe_2O_3$/$SiO_2$/$Fe_2O_3$/$SiO_2$/$Fe_2O_3$, a pigment having this structure being sold under the name Sicopearl by BASF; $MoS_2$/$SiO_2$/mica-oxide/$SiO_2$/$MoS_2$; $Fe_2O_3$/$SiO_2$/mica-oxide/$SiO_2$/$Fe_2O_3$; $TiO_2$/$SiO_2$/$TiO_2$ and $TiO_2$/$Al_2O_3$/$TiO_2$, pigments having these structures being sold under the name Xirona by Merck.

The liquid crystal colouring agents comprise, for example, silicones or cellulose ethers to which mesomorphic groups are grafted. Use may be made, as liquid crystal goniochromatic particles, for example, of those sold by Chenix and of those sold under the name Helicone® HC by Wacker.

Use may also be made, as goniochromatic pigment, of certain pearlescent agents, effect pigments on a synthetic substrate, in particular a substrate of alumina, silica, borosilicate, iron oxide or aluminium type, or interference glitter resulting from a polyterephthalate film.

Mention may in particular be made, as non-limiting examples of goniochromatic pigments, alone or as mixtures, of the goniochromatic pigments SunShine® sold by Sun, Cosmicolor Celeste® from Toyo Aluminium K.K., Xirona® from Merck and Reflecks Multidimensions® from BASF.

The composition according to the invention may also comprise one or more liposoluble or water-soluble dyes.

Among the liposoluble dyes, mention may be made especially of fluoran dyes such as, for example, red Sudan, FDC Red 4, DC Red 17, Red 21, Red 27, DC Green 6, Sudan brown, Yellow 10, DC Yellow 11, DC Violet 2, DC Orange 4, DC Orange 5, Yellow quinoline, or mixtures thereof.

Among the water-soluble dyes, mention may be made, among others, of synthetic or natural water-soluble dyes such as for example DC Red 6 (CI: 15850), DC Red 22 (CI: 45380), DC Red 28 (CI: 45410 Na salt), DC Red 30 (CI: 73360), DC Red 33 (CI: 17200), FDC Red 40 (CI 16035), FDC Yellow 5 (CI 19140), FDC Yellow 6 DC Yellow 8 (CI: 45350 Na Sel), FDC Green 3 (CI 42053), DC Green 5 (CI 61570), FDC Blue 1 (CI 42090).

As examples of sources of water-soluble dyes, mention may in particular be made of those of natural origin, such as extracts Carmine, cochineal, beet, grape, carrot, tomato, annatto, paprika, henna, caramel and curcumin.

Thus, the water-soluble dyes that can be used are in particular carminic acid, betanine, anthocyanins, enocyanines, lycopene, bixin, norbixin, capsanthyne, capsorubin, flovoxanthin, lutein, cryptoxanthin, Rubixanthin, violaxanthin, riboflavin, roudoxanthin, cantaxanthin, chlorophyll, and mixtures thereof.

It may also be copper sulfate, iron, water-soluble sulfopolyesters, rhodamine, betaine, methylene blue, disodium salt of tartrazine and disodium salt of fuschine.

For the purposes of the invention, the term "water-soluble dye" is understood to mean any compound which is soluble in an aqueous phase or water-miscible solvent, and which is capable of colouring (solubilization in water, at 25° C., concentration of at least 0.1 g/l, in particular greater than or equal to 1 g/l; a macroscopically isotropic and transparent solution, whether colored or not, is obtained).

Mineral Thickeners

The composition according to the invention can also comprise at least one mineral thickener chosen from optionally modified clays, optionally modified silicas, or their mixtures.

More particularly, if the competition contains it, the content of mineral thickener represents from 0.2% to 15% by weight, expressed as active material, and preferably from 0.5% to 7% by weight, with respect to the weight of the composition.

Optionally Modified Clays

Clays are silicates containing a cation which can be chosen from calcium, magnesium, aluminium, sodium, potassium or lithium cations, and their mixtures.

Mention may be made, as examples of such products, of clays of the family of the smectites, and also of the family of the vermiculites, stevensites or chlorites. These clays can be of natural or synthetic origin.

Preferably, use is made of organophilic clays, more particularly of modified clays, such as montmorillonite, bentonite, hectorite, attapulgite or sepiolite, and their mixtures. The clay is preferably a bentonite or a hectorite.

These clays are modified with a chemical compound chosen from quaternary amines, tertiary amines, amine acetates, imidazolines, amine soaps, fatty sulfates, alkylarylsulfonates or amine oxides, and their mixtures.

Mention may thus be made of hectorites modified by a quaternary amine, more specifically by a $C_{10}$ to $C_{22}$ fatty acid ammonium halide, such as a chloride, comprising or not comprising an aromatic group, such as hectorite modified by a distearyldimethylammonium halide, preferably a chloride, (CTFA name: Disteardimonium hectorite), such as, for example, that sold under the name Bentone 38V, Bentone 38V CG or Bentone EW CE by Elementis, or stearalkonium hectorites, such as in particular the product Bentone 27 V.

Mention may also be made of quaternium-18 bentonites, such as those sold, inter alia, under the names Bentone 34 by Elementis, Claytone 40, Tixogel VP by Southern Clay; stearalkonium bentonites, such as those sold under the names Tixogel LG by United Catalyst and Claytone AF and Claytone APA by Southern Clay; or quaternium-18/benzalkonium bentonites, such as those sold under the name Claytone HT by Southern Clay.

According to a preferred embodiment, the thickening agent is chosen from organophilic modified clays, in particular organophilic modified hectorites, in particular modified by benzyldimethylammonium stearate or distearyldimethylammonium halides, in particular chlorides.

In accordance with an alternative form of the invention, the content of optionally modified clay varies from 0.2% to 10% by weight, with respect to the weight of the composition, and preferably from 0.5% to 5% by weight, with respect to the weight of the composition. These percentages are expressed as active material.

Optionally Modified Silicas

Mention may also be made of fumed silica preferably hydrophobically treated at the surface, the size of the particles of which is advantageously less than 1 μm. This is because it is possible to chemically modify the surface of the silica, by chemical reaction generating a reduction in the number of silanol groups present at the surface of the silica. Silanol groups can in particular be replaced by hydrophobic groups: a hydrophobic silica is then obtained. The hydrophobic groups can be:

trimethylsiloxyl groups, which are obtained in particular by treatment of fumed silica in the presence of hexamethyldisilazane. Silicas thus treated are known as Silica Silylate according to the CTFA (6th edition, 1995). They are sold, for example, under the references Aerosil R812® by Degussa and Cab-O-Sil TS-530® by Cabot, dimethylsilyloxyl or polydimethylsiloxane groups, which are obtained in particular by treatment of fumed silica in the presence of polydimethylsiloxane or dimethyldichlorosilane. Silicas thus treated are known as Silica Dimethyl Silylate according to the CTFA (6th edition, 1995). They are sold, for example, under the references Aerosil R972® and Aerosil R974® by Degussa and Cab-O-Sil TS-610® and Cab-O-Sil TS-720® by Cabot.

The hydrophobic fumed silica exhibits in particular a particle size which can be nanometric to micrometric, for example ranging from approximately 5 to 200 nm.

The composition according to the invention can also comprise at least silica aerogel particles.

Silica aerogels are porous materials obtained by replacing (by drying) the liquid component of a silica gel with air.

They are generally synthesized by a sol-gel process in a liquid medium and then dried, usually by extraction with a supercritical fluid, the one most commonly used being supercritical $CO_2$. Drying of this type makes it possible to avoid contraction of the pores and of the material. The sol-gel process and the various drying operations are described in detail in Brinker C. J. and Scherer G. W., Sol-Gel Science, New York, Academic Press, 1990.

The hydrophobic silica aerogel particles suitable for the implementation of the invention exhibit a specific surface per unit of weight ($S_w$) ranging from 500 to 1500 $m^2/g$, preferably from 600 to 1200 $m^2/g$ and better still from 600 to 800 $m^2/g$, and a size, expressed as the volume-average diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to an advantageous embodiment, the hydrophobic silica aerogel particles used in the present invention exhibit a specific surface per unit of weight ($S_w$) ranging from 600 to 800 $m^2/g$ and a size, expressed as volume-average diameter (D[0.5]), ranging from 5 to 20 μm and even better still from 5 to 15 ƒm.

The specific surface per unit of weight can be determined by the nitrogen absorption method, known as the BET (Brunauer-Emmett-Teller) method, described in The Journal of the American Chemical Society, Vol. 60, page 309, February 1938, which corresponds to International Standard ISO 5794/1 (Appendix D). The BET specific surface corresponds to the total specific surface of the particles under consideration.

The sizes of the silica aerogel particles can be measured by static light scattering using a commercial particle size analyser of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., Light Scattering by Small Particles, Chapters 9 and 10, Wiley, New York, 1957.

According to a preferred embodiment, the hydrophobic silica aerogel particles used in the present invention exhibit a specific surface per unit of volume $S_V$ ranging from 5 to 60 $m^2/cm^3$, preferably from 10 to 50 $m^2/cm^3$ and better still from 15 to 40 $m^2/cm^3$.

The aerogels which can be used according to the present invention are aerogels of hydrophobic silica, preferably of silylated silica (INCI name: Silica Silylate).

As regards the preparation of hydrophobic silica aerogel particles modified at the surface by silylation, reference may be made to the document U.S. Pat. No. 7,470,725.

Use will preferably be made of hydrophobic silica aerogel particles modified at the surface by trimethylsilyl groups.

Mention may be made, as hydrophobic silica aerogels which can be used in the invention, for example, of the aerogel sold under the name VM-2260 (INCI name: Silica Silylate) by Dow Corning, the particles of which exhibit an average size of approximately 1000 microns and a specific surface per unit of weight ranging from 600 to 800 $m^2/g$.

Mention may also be made of the aerogels sold by Cabot under the references Aerogel TLD 201, Aerogel OGD 201, Aerogel TLD 203, Enova® Aerogel MT 1100 and Enova Aerogel MT 1200.

Use will preferably be made of the aerogel sold under the name VM-2270 (INCI name: Silica Silylate) by Dow Corning, the particles of which exhibit an average size ranging from 5 to 15 microns and a specific surface per unit of weight ranging from 600 to 800 $m^2/g$.

Preferably, when the composition comprises at least one thickening agent chosen from optionally modified silicas, the latter are chosen from hydrophobic silica aerogel particles.

In accordance with an alternative form of the invention, the content of optionally modified silica varies from 0.5% to 15% by weight and preferably from 1% to 7% by weight, with respect to the weight of the composition. These values are expressed as weight of active material.

Preferably, the mineral thickeners are chosen from organophilic clays, in particular modified hectorites; hydrophobic treated fumed silica; hydrophobic silica aerogels, or their mixtures, and more specifically still at least one organophilic modified clay or at least one hydrophobic modified silica, in particular hydrophobic silica aerogels.

Fillers

The composition according to the invention can also comprise at least one filler.

"Filler" denotes a particle of organic or inorganic nature which is colourless or white, which is solid, which has any shape and which is insoluble in the medium of the composition at ambient temperature and atmospheric pressure. These fillers are advantageously dispersed in the composition.

"Inorganic" is understood to mean any compound, the chemical structure of which does not comprise a carbon atom.

The fillers may or may not be surface-coated, and in particular they can be surface-treated with silicones, amino acids, fluorinated derivatives or any other substance which promotes the dispersion and compatibility of the filler in the composition.

Such fillers are distinct from the mineral thickeners and also from the colouring agents described above.

The fillers can be spherical, that is to say comprise at least a rounded general portion, preferably defining at least a sphere portion, preferably internally defining a concavity or a hollow (sphere, globules, bowls, horseshoe, and the like), or lamellar.

Such fillers are advantageously chosen from:

silica powders, such as the porous silica microspheres sold under the name Silica Beads SB-700 by Miyoshi or Sunsphere® H-51 or Sunsphere® H-33 by Asahi Glass; or the polydimethylsiloxane-coated amorphous silica microspheres sold under the name SA Sunsphere® H-33 or SA Sunsphere® H-53 by Asahi Glass, powders of acrylic (co)polymers and their derivatives, in particular:

the polymethyl methacrylate powder sold under the names Covabead® LH85 by Wackherr or Microsphere M-100® by Matsumoto, the polymethyl methacrylate/ethylene glycol dimethacrylate powder sold under the name Dow Corning 5640 Microsponge® Skin Oil Adsorber by Dow Corning or Ganzpearl® GMP-0820 by Ganz Chemical, the polyallyl methacrylate/ethylene glycol dimethacrylate powder sold under the name Poly-Pore® L200 or Poly-Pore® E200 by Amcol Health and Beauty Solutions Inc., the ethylene glycol dimethacrylate/lauryl methacrylate copolymer powder sold under the name Polytrap® 6603 by Dow Corning, the optionally crosslinked acrylate/alkyl acrylate copolymer crosslinked acrylate/ethylhexyl acrylate copolymer powder sold under the name Techpolymer ACP-8C by Sekisui Plastics, ethylene/acrylate copolymer powder, such as that sold under the name Flobeads® by Sumitomo Seika Chemicals, the expanded hollow particles of acrylonitrile (co)polymer sold under the name Expancel by Expancel or the microspheres sold under the name Micropearl F 80 ED® by Matsumoto, polyurethane powders, for example sold under the names Plastic Powder D-400, Plastic Powder CS-400, Plastic Powder D-800 and Plastic Powder T-75 by Toshiki, silicone powders advantageously chosen from:

polymethylsilsesquioxane powders, in particular those sold under the name Tospearl, in particular Tospearl 145 A, by Momentive Performance Materials, organopolysiloxane elastomer powders coated with silicone resin, in particular with silsesquioxane resin, such as the products sold under the name KSP-100, KSP-101, KSP-102, KSP-103, KSP-104 or KSP-105 by Shin-Etsu (INCI name: vinyl dimethicone/methicone silsesquioxane crosspolymer), powders of silicone elastomers, such as the products sold under the name Trefil® Powder E-505C or Trefil® Powder E-506C by Dow Corning, powders of organosilicone particles, for example, in the form of bowls, such as those described in JP-2003 128 788 or JP-A-2000-191789 or also in Application EP 1 579 841 and sold in particular by Takemoto Oil & Fat, polyamide powders, such as Nylon® powders, in particular Nylon 12 powders, such as the nylon powders sold under the name Orgasol® 2002 EXS NAT COS by Arkema, powders of natural organic materials, such as polysaccharide powders and in particular starch powders, especially crosslinked or non-crosslinked maize, wheat or rice starch powders, powders of starch crosslinked by octenylsuccinic anhydride sold under the name Dry-Flo® by National Starch or powders of waxy maize starch, such as those which are sold under the names C* Gel 04201 by Cargill, Maize Starch B by Roquette and Organic Corn Starch by Draco Natural Products, spherical cellulose microparticles, such as Cellulobeads D-10, Cellulobeads D-5 and Cellulobeads USF, sold by Daito Kasei Kogyo, particles of N—($C_8$-$C_{22}$ acylated) amino acids; the amino acid can, for example, be lysine, glutamic acid or alanine, preferably lysine, for example Amihope LL from Ajinomoto or also that which is sold under the name Corum 5105 S by Corum, Perlite powders, such as those sold by World Minerals under the trade name Perlite P1430, Perlite P2550, Perlite P2040 or OpTiMat™ 1430 OR or 2550 OR, Europerl EMP-2 and Europerl 1 by Imerys, zeolites, such as the products sold by Zeochem under the names Zeoflair 300, Zeoflair 200, Zeoflair 100, X-Mol and X-Mol MT, calcium magnesium carbonate particles, such as those sold by Imerys under the name Calcidol, by LCW (Sensient) under the name Carbomat or by Omya under the name Omyacare S60-AV.

Use may also be made of talc particles, for example sold under the names Luzenac Pharma M and UM by Imerys and Rose Talc and Talc SG-2000 by Nippon Talc; natural or synthetic mica particles, such as those sold under the names Mica M RP and Silk Mica by Merck or also that sold under the name Sericite S-152-BC by Miyoshi Kasei; calcium carbonate and magnesium hydrogencarbonate; hydroxyapatite; boron nitride; fluorphlogopite; and their mixtures.

The spherical fillers can be coated with a hydrophobic treatment agent. The hydrophobic treatment agent can be chosen from fatty acids, such as stearic acid; metal soaps, such as aluminium dimyristate or the aluminium salt of hydrogenated tallow glutamate; amino acids; N-acylated amino acids or their salts; lecithin; isopropyl triisostearyl titanate; and their mixtures. The N-acylated amino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be the aluminium, magnesium, calcium, zirconium, zinc, sodium or potassium salts. The amino acid can, for example, be lysine, glutamic acid or alanine. The term "alkyl" cited in the abovementioned compounds denotes in particular an alkyl group having from 1 to 30 carbon atoms and preferably having from 5 to 16 carbon atoms.

If the composition according to the invention contains it/them, the content of filler(s) advantageously represents from 0.5% to 15% by weight and more particularly from 2% to 10% by weight, with respect to the weight of the composition.

Optional Additives

The composition can comprise at least one optional additive chosen, for example, from film-forming agents; antioxidants; preservatives; fragrances; flavourings; neutralizing agents; emollients; organic thickeners; coalescence agents; moisturizing agents; vitamins; and their mixtures.

Of course, a person skilled in the art will take care to choose the optional additional additives and/or their amounts in such a way that the advantageous properties of the composition according to the invention are not, or not substantially, detrimentally affected by the envisaged addition.

The examples which follow serve to illustrate the invention without, however, limiting the scope thereof.

EXAMPLES

Example 1

The following compositions, the ingredients of which and their respective contents are collated in the table below, are prepared (the contents are expressed as % by weight of starting material, unless otherwise indicated):

| Phase | Ingredients (chemical name or INCI name) | Composition 1 | Composition 2 |
|---|---|---|---|
| A | Octyldodecanol | 20 | 53.1 |
|  | Coco-caprylate/caprate (Cetiol LC, BASF)** | 29.4 | — |
|  | Ethylcellulose (Aqualon EC N7 Pharm, Ashland) | 12.6 | 13.9 |
| B | $TiO_2$ Rutile | 1.8 | 1.8 |
|  | Red 28 lake | 1.3 | 1.3 |
|  | Red 7 | 1.5 | 1.5 |
|  | Yellow 6 lake | 2.0 | 2.0 |
|  | Iron oxide | 1.4 | 1.4 |
| C | Trimethylsiloxyphenyl dimethicone (Belsil PDM 1000; Wacker) | 30 | 25 |
|  | Ethylcellulose/ethylcellulose + octyldodecanol ratio by weight* | 38.6% | 20.7% |

*Calculation: [content of ethylcellulose/(content of ethylcellulose + octyldodecanol)]*100
**oil compatible with the octyldodecanol Preparation of the Compositions:

The pigments are ground in a portion of the octyldodecanol.

The ethylcellulose is dispersed in the remainder of the octyldodecanol and the coco-caprylate/caprate, if this compound is present, at 105° C., with Rayneri stirring (speed of the stirring sufficient to have a vortex).

Once the ethylcellulose has dissolved, the pigments/octyldodecanol mixture is added, under the same temperature and stirring conditions.

Finally, after homogenization, the silicone is added, at 105° C., with Rayneri stirring, over at least 15 minutes.

The resulting mixture is poured under hot conditions into the conditioning jar.

Evaluation of the Compositions:

Wear of Colour:

The wear-property index of the deposited layer obtained with each composition is determined according to the measurement protocol described below:

A support (40 mm×70 mm rectangle) consisting of an acrylic coating (hypoallergenic acrylic adhesive on polyethylene film sold under the name Blenderme Ref FH5000-55113 by 3M Santé) bonded to a layer of polyethylene foam which is adhesive on the face opposite that to which the adhesive plaster is fixed (foam layer sold under the name RE 40X70EP3 from Joint Technique Lyonnais Ind.) is prepared.

The colour $L*0a*0b*0$ of the support, on the acrylic coating face side, is measured using a Minolta CR300 colourimeter.

The support thus prepared is preheated on a hotplate maintained at a temperature of 40° C. so that the surface of the support is maintained at a temperature of 33° C.±1° C.

While leaving the support on the hotplate, the composition is applied to the entire non-adhesive surface of the support (that is to say to the surface of the acrylic coating), spreading it out using a brush in order to obtain a deposited layer of the composition of approximately 15 μm, and then drying is allowed to take place for 10 minutes.

After drying, the $L*a*b*$ colour of the film thus obtained is measured.

The colour difference ΔE1 between the colour of the film with respect to the colour of the bare support is then determined by the following relationship:

$$\Delta E1=(L*-Lo*)2+(a*-ao*)2+(b*-bo*)2$$

The support is subsequently bonded via its adhesive face (adhesive face of the foam layer) to an anvil 20 mm in diameter and equipped with a screw pitch.

A test specimen of the support/deposited layer assembly is subsequently cut out using a hollow punch 18 mm in diameter. The anvil is subsequently screwed onto a press (Statif Manuel Imada SV-2 from Someco) equipped with a tensile testing device (Imada DPS-20 from Someco).

A strip 33 mm wide and 29.7 cm long is drawn on a sheet of white photocopier paper with a basis weight of 80 g/m², a first line is marked out at 2 cm from the edge of the sheet and then a second line is marked out at 5 cm from the edge of the sheet, the first and second lines thus delimiting a box on the strip; next, a first mark and a second mark, located in the strip at the reference points respectively 8 cm and 16 cm from the second line, are applied.

The sheet of white paper is placed on the base of the press and then the test specimen placed on the box of the strip of paper is pressed at a pressure of approximately 300 g/cm² exerted for 30 seconds. The press is then opened and the test specimen is again placed just after the second line (thus next to the box), a pressure of approximately 300 g/cm² is again exerted, and the sheet of paper is displaced, in a rectilinear manner as soon as contact is made, with a speed of 1 cm/s over the entire length of the strip.

After removing the test specimen, a portion of the deposited layer has transferred onto the paper.

The $L*'$, $a*'$, $b*'$ colour of the deposited layer remaining on the test specimen is then measured. The colour difference ΔE2 between the colour of the deposited layer remaining on the test specimen with respect to the colour of the bare support is then determined by the following relationship:

$$\Delta E2=(L*'-Lo*)2+(a*'-ao*)2+(b*'-bo*)2$$

The wear-property index of the composition, expressed as a percentage, is equal to the ratio:

$$100 \times \Delta E2/\Delta E1$$

The measurement is carried out on 6 supports in succession and the wear-property value corresponds to the mean of the 6 measurements obtained with the 6 supports.

Viscosity:

The viscosity at 25° C. of the compositions was evaluated according to the protocol described above in the description.

Stability:

The stability of the compositions is evaluated by storing the composition for 72 hours at ambient temperature and by observing whether separation of the oily phase and/or sedimentation of the pigments and/or pearlescent agents takes place.

Gloss:

The gloss of the deposited layer obtained on the lips with composition can be evaluated using a Polka SEI-M-0216-Polk-02 polarimetric camera and a Chromasphere SEI-M-02232-CHRO-0, as described in Application FR 2 829 344.

The gloss is evaluated immediately after application, and 1 hour after application of the formula.

The formulation is applied to the lips of a panel of six subjects exhibiting thick and thin lips.

The gloss of the deposited layers which are obtained with the compositions can also be evaluated visually by applying the composition to the lips, immediately after application and 1 hour after application.

Results:

|  | Composition 1 | Composition 2 |
|---|---|---|
| Appearance of the composition | Homogeneous, no exudation of oil, stable | Homogeneous, no exudation of oil, stable |
| Viscosity | 20 Pa · s | 21 Pa · s |
| Stability | Stable | Stable |
| Deposited layer | Homogeneous, non-tacky, does not dry out the lips, without feeling of tightness | Homogeneous, non-tacky, does not dry out the lips, without feeling of tightness |
| Gloss and wear of gloss | Good gloss which lasts over time | Good gloss which lasts over time |
| Wear of colour | Non-transfer of the colour | Non-transfer of the colour |

Example 2

The following compositions, the ingredients of which and their respective contents are collated in the table below, are prepared (the contents are expressed as % by weight of starting material, unless otherwise indicated):

| Phase | Ingredients (chemical name or INCI name) | Composition 3 | Composition 4 |
|---|---|---|---|
| A | Octyldodecanol | 18.7 | 18.7 |
|  | Coco-caprylate/caprate (Cetiol LC, BASF) | 21.9 | 21.9 |
|  | Ethylcellulose (Aqualon EC N7 Pharm, Ashland) | 9.4 | 9.4 |
| B | $TiO_2$ Rutile | 1.8 | 1.8 |
|  | Red 28 lake | 1.3 | 1.3 |
|  | Red 7 | 1.5 | 1.5 |
|  | Yellow 6 lake | 2.0 | 2.0 |
|  | Iron oxide | 1.4 | 1.4 |
| C | Trimethylsiloxyphenyl dimethicone (Belsil PDM 1000; Wacker) | 30 | 30 |
|  | $C_{30-50}$ alcohols (Performacol 550 Alcohol; New Phase Technologies) | 12 | — |
|  | Polyethylene wax | — | 12 |
|  | Ethylcellulose/ethylcellulose + octyldodecanol ratio by weight* | 33.5% | 33.5% |

*Calculation: [content of ethylcellulose/(content of ethylcellulose + octyldodecanol)]*100

Preparation of the Compositions:

The pigments are ground in a portion of the octyldodecanol.

The ethylcellulose is dispersed in the remainder of the octyldodecanol, at 105° C., with Rayneri stirring (speed of the stirring sufficient to have a vortex).

Once the ethylcellulose has dissolved, the pigments/octyldodecanol mixture and the wax are added, under the same temperature and stirring conditions.

Finally, after homogenization, the silicone is added, at 105° C., with Rayneri stirring, over at least 15 minutes.

The resulting mixture is poured under hot conditions into the lipstick mould preheated to 42° C. and the assembly is cooled down to 4° C. Finally, the composition is removed from the mould and the sticks are conditioned.

Evaluation of the Compositions:

Wear of Colour:

The evaluation method is that described in the preceding examples.

Stability:

The stability of the compositions is evaluated by storing the composition at ambient temperature for 72 hours and by observing if there is exudation of one or more oils.

Hardness:

The hardness is measured according to the protocol defined above in the description.

Gloss:

The evaluation method is that described in the preceding examples.

Results:

|  | Composition 3 | COMPOSITION 4 |
|---|---|---|
| Appearance of the composition | Homogeneous, no exudation of oil, stable | Homogeneous, no exudation of oil, stable |
| Hardness | 47.8 $Nm^{-1}$ | 72.5 $Nm^{-1}$ |
| Deposited layer | Homogeneous, non-tacky, does not dry out the lips, without feeling of tightness | Homogeneous, non-tacky, does not dry out the lips, without feeling of tightness |
| Gloss and wear of gloss | Good gloss which lasts over time | Good gloss which lasts over time |
| Wear of colour | Non-transfer of the colour | Non-transfer of the colour |

Example 3

The following compositions, the ingredients of which and their respective contents are collated in the table below, are prepared (the contents are expressed as % by weight of starting material, unless otherwise indicated):

| Phase | Ingredients (chemical name or INCI name) | Composition 5 invention |
|---|---|---|
| A | Octyldodecanol | 18.7 |
|  | Coco-caprylate/caprate (Cetiol LC, BASF)** | 21.9 |
|  | Hydrogenated jojoba oil (Jojoba Wax Flakes; Desert Whale) | 12 |
|  | Ethylcellulose (Aqualon EC N7 Pharm, Ashland) | 9.4 |
| B | $TiO_2$ Rutile | 1.8 |
|  | Red 28 lake | 1.3 |
|  | Red 7 | 1.5 |
|  | Yellow 6 lake | 2.0 |
|  | Iron oxide | 1.4 |
| C | Trimethylsiloxyphenyl dimethicone (Belsil PDM 1000; Wacker) | 30 |

-continued

| Phase | Ingredients (chemical name or INCI name) | Composition 5 invention |
|---|---|---|
| | Ethylcellulose/ethylcellulose + octyldodecanol ratio by weight* | 33.5% |

*Calculation: [content of ethylcellulose/(content of ethylcellulose + octyldodecanol)]*100
**Oil compatible with the octyldodecanol Preparation of the Compositions:

The pigments are ground in a portion of the octyldodecanol.

The ethylcellulose is dispersed in the remainder of the octyldodecanol, and in the coco-caprylate/caprate, at 105° C., with Rayneri stirring (speed of the stirring sufficient to have a vortex).

Once the ethylcellulose has dissolved, the pigments/octyldodecanol mixture and the wax are added, under the same temperature and stirring conditions.

Finally, after homogenization, the silicone is added, at 105° C., with Rayneri stirring, over at least 15 minutes.

The mixture is cooled with Rayneri stirring down to ambient temperature.

Results:

Viscosity

The viscosity at 25° C. of the compositions was evaluated according to the protocol described above.

Stability

The stability of the compositions is evaluated by storing the composition for 72 hours at ambient temperature and by observing whether separation of the oily phase and/or sedimentation of the pigments and/or pearlescent agents takes place.

| | Composition 5 |
|---|---|
| Appearance of the composition | Homogeneous, no exudation of oil, stable |
| Viscosity | 20 Pa · s |
| Deposited layer | Homogeneous, non-tacky, does not dry out the lips, without feeling of tightness |
| Gloss and wear of gloss | Very good gloss |
| Wear of colour | Non-transfer of the colour |

Examples 4 and Comparative 5

The following compositions, the ingredients of which and their respective contents are collated in the table below, are prepared (the contents are expressed as % by weight of starting material, unless otherwise indicated):

| Phase | Ingredients (chemical name or INCI name) | Composition 6 | Comparative composition 7 |
|---|---|---|---|
| A | Octyldodecanol | 53.1 | 53.1 |
| | Ethylcellulose (Aqualon EC N7 Pharm, Ashland) | 13.9 | 13.9 |
| B | TiO$_2$ Rutile | 1.8 | 1.8 |
| | Red 28 lake | 1.3 | 1.3 |
| | Red 7 | 1.5 | 1.5 |
| | Yellow 6 lake | 2 | 2 |
| | Iron oxide | 1.4 | 1.4 |
| C | Trimethylsiloxyphenyl dimethicone (Belsil PDM 1000; Wacker) | 25 | — |
| | Phenyl trimethicone (DOW CORNING 556 COSMETIC GRADE FLUID) | — | 25 |
| | Ethylcellulose/ethylcellulose + octyldodecanol ratio by weight* | 20.7% | 20.7% |

Preparation of the Compositions:

The pigments are ground in a portion of the octyldodecanol.

The ethylcellulose is dispersed in the remainder of the octyldodecanol, at 105° C., with Rayneri stirring (speed of the stirring sufficient to have a vortex).

Once the ethylcellulose has dissolved, the pigments/octyldodecanol mixture is added, under the same temperature and stirring conditions.

Finally, after homogenization, the silicone is added, at 105° C., with Rayneri stirring, over at least 15 minutes.

The mixture is cooled with Rayneri stirring down to ambient temperature.

Results:

Viscosity, stability, gloss and wear of colour are evaluated as previously described.

| | Composition 6 | Composition 7 comparative |
|---|---|---|
| Appearance of the composition | Homogeneous, no exudation of oil, stable | Homogeneous, no exudation of oil, stable |
| Viscosity | 21 Pa · s | 22 Pa · s |
| Deposited layer | Homogeneous, non-tacky, does not dry out the lips, without feeling of tightness | Homogeneous, does not dry out the lips, but tacky and with a feeling of tightness |
| Gloss and wear of gloss | Good gloss which lasts over time | Good gloss which lasts over time |
| Wear of colour | Non-transfer of the colour | Transfer of the colour |

It is found that the comparative composition, which does not contain an incompatible silicone oil, is tackier and leaves a feeling of tightness. In addition the wear of colour is degraded.

The invention claimed is:

1. A cosmetic composition comprising:
    at least 2% by weight of alkylcellulose, wherein the alkylcellulose is ethylcellulose,
    at least one non-volatile polar hydrocarbon first oil, wherein the non-volatile polar hydrocarbon oil is octyldodecanol,
    at least 20% by weight, with respect to the weight of the composition, of at least one second oil, incompatible with the first oil or oils, chosen from non-volatile non-phenylated silicone oils, non-volatile phenylated silicone oils comprising at least one dimethicone fragment, and their combinations, and
    optionally at least one non-volatile third oil, different from the first oil or oils, chosen from polar or non-polar hydrocarbon oils, silicone oils different from the second oil or oils, phenylated oils not comprising a dimethicone fragment, or their mixtures,
    wherein the composition is anhydrous and wherein the composition is in a fluid form at 25° C.

2. The composition according to claim 1, wherein a content of ethylcellulose is between 2% and 16% by weight, with respect to the weight of the composition.

3. The composition according to claim 1, wherein the composition comprises at least one wax.

4. The composition according to claim 3, wherein the wax is chosen from polar or non-polar hydrocarbon waxes.

5. The composition according to claim 3, wherein a content of wax varies from 0.5% to 20% by weight, with respect to the weight of the composition.

6. The composition according to claim 1, further comprising at least one nonvolatile hydrocarbon first oil chosen from non-aromatic, saturated or unsaturated, linear or branched mono- or diesters comprising up to 30 carbon atoms and optionally comprising one or two ether groups; aromatic mono- or diesters comprising up to 30 carbon atoms and optionally comprising one or two ether groups; non-aromatic, saturated or unsaturated, linear or branched triesters comprising less than 60 carbon atoms and optionally comprising one to three ether groups; vegetable oils; and their mixtures.

7. The composition according to claim 1, wherein a content of octyldodecanol represents from 20% to 60% by weight, with respect to the weight of the composition.

8. The composition according to claim 1, wherein a ethylcellulose: (ethylcellulose+octyldodecanol)*100 ratio by weight varies from 10 to 60. oil(s) are chosen from non-volatile non-phenylated silicone oils, non-volatile phenylated silicone oils comprising at least one dimethicone fragment, and their combinations.

9. The composition according to claim 1, wherein a content of non-volatile silicone second oil(s) represents from 20% to 50% by weight, with respect to the weight of the composition.

10. The composition according to claim 1, wherein a content of third oil(s) represents from 5% and 40% by weight, with respect to the weight of the composition.

11. The composition according to claim 1, wherein the composition further comprises at least one volatile hydrocarbon, volatile silicone oil or their combinations.

12. The composition according to claim 11, wherein a content of volatile oil(s) represents from 5% to 30% by weight, with respect to the weight of the composition.

13. The composition according to claim 1, wherein the composition further comprises at least one compound which is pasty at ambient temperature and atmospheric pressure.

14. The composition according to claim 13, wherein a content of pasty compound varies from 0.5% to 15% by weight, with respect to the weight of the composition.

15. The composition according to claim 1, wherein the composition further comprises at least one colourant.

\* \* \* \* \*

UNITED STATES PATENT AND TRADEMARK OFFICE
CERTIFICATE OF CORRECTION

PATENT NO. : 11,351,105 B2  
APPLICATION NO. : 16/060059  
DATED : June 7, 2022  
INVENTOR(S) : Lahousse et al.

Page 1 of 1

It is certified that error appears in the above-identified patent and that said Letters Patent is hereby corrected as shown below:

In the Claims

In Column 41, Claim 8, Lines 24-25, delete "oil(s) are chosen from non-volatile non-phenylated silicone oils, non-volatile phe-".

In Column 42, Claim 8, Lines 1-2, delete "nylated silicone oils comprising at least one dimethicone fragment, and their combinations.".

Signed and Sealed this  
Twenty-ninth Day of November, 2022

Katherine Kelly Vidal  
*Director of the United States Patent and Trademark Office*